(12) United States Patent
Dubois et al.

(10) Patent No.: US 9,770,289 B2
(45) Date of Patent: Sep. 26, 2017

(54) VACUUM POWERED ROTARY DEVICES AND METHODS

(71) Applicant: Laurimed, LLC, Redwood City, CA (US)

(72) Inventors: Brian R. Dubois, Redwood City, CA (US); James T. Nielsen, San Francisco, CA (US); Alexander Gordon, Menlo Park, CA (US)

(73) Assignee: Myromed, LLC, Redwood City, CA (US)

( * ) Notice: Subject to any disclaimer, the term of this patent is extended or adjusted under 35 U.S.C. 154(b) by 595 days.

(21) Appl. No.: 13/734,828

(22) Filed: Jan. 4, 2013

(65) Prior Publication Data

US 2013/0218186 A1    Aug. 22, 2013

Related U.S. Application Data

(60) Provisional application No. 61/597,648, filed on Feb. 10, 2012, provisional application No. 61/684,656, filed on Aug. 17, 2012.

(51) Int. Cl.
| | |
|---|---|
| *A61B 17/14* | (2006.01) |
| *A61B 18/14* | (2006.01) |
| *A61B 17/32* | (2006.01) |
| *A61B 17/3205* | (2006.01) |

(Continued)

(52) U.S. Cl.
CPC ............ *A61B 18/148* (2013.01); *A61B 17/32* (2013.01); *A61B 17/32002* (2013.01); *A61B 17/32053* (2013.01); *A61B 2017/0023* (2013.01); *A61B 2017/00544* (2013.01); *A61B 2017/320024* (2013.01); *A61B 2017/320064* (2013.01); *A61B 2018/00577* (2013.01); *A61B 2018/00595* (2013.01); *A61B 2217/005* (2013.01)

(58) Field of Classification Search
CPC ...... A61B 17/32002; A61B 17/320758; A61B 18/04; A61B 17/14
USPC ............................ 606/115, 177, 180; 604/26
See application file for complete search history.

(56) References Cited

U.S. PATENT DOCUMENTS

| | | | |
|---|---|---|---|
| 1,527,291 | A | 2/1925 | Zorraquin |
| 1,733,502 | A | 10/1929 | Linsley |
| 2,895,455 | A | 7/1959 | Clowes |

(Continued)

FOREIGN PATENT DOCUMENTS

| | | |
|---|---|---|
| EP | 1002500 | 5/2000 |
| EP | 0746245 | 11/2002 |

(Continued)

OTHER PUBLICATIONS

U.S. Appl. No. 11/838,675, filed Aug. 14, 2007.

(Continued)

*Primary Examiner* — Victor Nguyen
(74) *Attorney, Agent, or Firm* — Levine Bagade Han LLP

(57) ABSTRACT

The present devices and methods relate generally to vacuum or suction powered medical devices and methods for cutting, resecting, excising, morcellating and/or evacuating tissue from various regions of a patient's body. In certain variations, the devices may produce a rotational motion by converting a linear reciprocating motion to a rotational motion, causing a cutting shaft or other tool to rotate to perform work on a tissue in various regions of the body.

23 Claims, 22 Drawing Sheets

(51) Int. Cl.
*A61B 17/00* (2006.01)
*A61B 18/00* (2006.01)

(56) References Cited

U.S. PATENT DOCUMENTS

| | | |
|---|---|---|
| 3,081,770 A | 3/1963 | Hunter |
| 3,401,684 A | 9/1968 | Dremann |
| 3,469,580 A | 9/1969 | Huddy |
| 3,561,429 A | 2/1971 | Jewett et al. |
| 3,682,162 A | 8/1972 | Colyer |
| 3,689,955 A | 9/1972 | Winkelmann |
| 3,709,211 A | 1/1973 | Hawkins |
| 3,782,381 A | 1/1974 | Winnie |
| 3,809,093 A | 5/1974 | Abraham |
| 3,815,604 A | 6/1974 | O'Malley et al. |
| 3,884,238 A | 5/1975 | O'Malley et al. |
| 3,941,127 A | 3/1976 | Froning |
| 3,943,932 A | 3/1976 | Woo |
| 3,977,400 A | 8/1976 | Moorehead |
| 4,013,080 A | 3/1977 | Froning |
| 4,068,659 A | 1/1978 | Moorehead |
| 4,192,319 A | 3/1980 | Hargens et al. |
| 4,314,560 A | 2/1982 | Helfgott et al. |
| RE30,966 E | 6/1982 | Hargens et al. |
| 4,349,023 A | 9/1982 | Gross |
| 4,368,730 A | 1/1983 | Sharrock |
| 4,428,748 A | 1/1984 | Peyman et al. |
| 4,434,053 A | 2/1984 | Osuna et al. |
| 4,507,167 A | 3/1985 | Jahme et al. |
| 4,511,356 A | 4/1985 | Froning et al. |
| 4,512,351 A | 4/1985 | Pohndorf |
| 4,518,383 A | 5/1985 | Evans |
| 4,580,573 A | 4/1986 | Quinn |
| 4,588,399 A | 5/1986 | Nebergall et al. |
| 4,609,370 A | 9/1986 | Morrison |
| 4,662,869 A | 5/1987 | Wright |
| 4,678,459 A | 7/1987 | Onik et al. |
| 4,721,506 A | 1/1988 | Teves |
| 4,737,146 A | 4/1988 | Amaki et al. |
| 4,775,637 A | 10/1988 | Sutherland et al. |
| 4,808,157 A | 2/1989 | Coombs |
| 4,842,585 A | 6/1989 | Witt |
| 4,846,799 A | 7/1989 | Tanaka et al. |
| 4,886,067 A | 12/1989 | Palermo |
| 4,886,492 A | 12/1989 | Brooke |
| 4,917,668 A | 4/1990 | Haindl |
| 4,917,670 A | 4/1990 | Hurley et al. |
| RE33,258 E | 7/1990 | Onik et al. |
| 4,940,458 A | 7/1990 | Cohn |
| 4,958,901 A | 9/1990 | Coombs |
| 4,973,305 A | 11/1990 | Goltzer |
| 4,973,312 A | 11/1990 | Andrew |
| 4,994,036 A | 2/1991 | Biscoping et al. |
| 5,004,456 A | 4/1991 | Botterbusch et al. |
| 5,007,902 A | 4/1991 | Witt |
| 5,024,655 A | 6/1991 | Freeman et al. |
| 5,026,350 A | 6/1991 | Tanaka et al. |
| 5,060,658 A | 10/1991 | Dejter, Jr. et al. |
| 5,078,679 A | 1/1992 | Reese |
| 5,085,631 A | 2/1992 | Leighton |
| 5,085,659 A | 2/1992 | Rydell |
| 5,098,388 A | 3/1992 | Kulkashi et al. |
| 5,100,379 A | 3/1992 | Wendell |
| 5,100,390 A | 3/1992 | Lubeck et al. |
| 5,106,376 A | 4/1992 | Mononen et al. |
| 5,119,832 A | 6/1992 | Xavier |
| 5,129,889 A | 7/1992 | Hahn et al. |
| 5,135,525 A | 8/1992 | Biscoping et al. |
| 5,152,744 A | 10/1992 | Krause et al. |
| 5,160,323 A | 11/1992 | Andrew |
| 5,163,901 A | 11/1992 | Eldor |
| 5,176,628 A | 1/1993 | Charles et al. |
| 5,205,828 A | 4/1993 | Kedem |
| 5,207,647 A | 5/1993 | Phelps |
| 5,209,734 A | 5/1993 | Hurley et al. |
| 5,213,578 A | 5/1993 | Heiliger et al. |
| 5,232,442 A | 8/1993 | Johnson et al. |
| 5,234,406 A | 8/1993 | Drasner et al. |
| 5,257,972 A | 11/1993 | Gurmarnik |
| 5,263,936 A | 11/1993 | Yurino |
| 5,269,769 A | 12/1993 | Dhara et al. |
| 5,292,310 A | 3/1994 | Yoon |
| 5,304,141 A | 4/1994 | Johnson et al. |
| 5,306,239 A | 4/1994 | Gurmarnik et al. |
| 5,312,374 A | 5/1994 | Gurmarnik |
| 5,312,375 A | 5/1994 | Gurmarnik |
| 5,320,610 A | 6/1994 | Yoon |
| 5,328,479 A | 7/1994 | Gurmarnik |
| 5,335,671 A | 8/1994 | Clement |
| 5,368,573 A | 11/1994 | Andrew |
| 5,376,082 A | 12/1994 | Phelps |
| 5,385,561 A | 1/1995 | Cerny |
| 5,392,790 A | 2/1995 | Kanner et al. |
| 5,405,334 A | 4/1995 | Roth et al. |
| 5,417,208 A | 5/1995 | Winkler |
| 5,423,760 A | 6/1995 | Yoon |
| 5,423,770 A | 6/1995 | Yoon |
| 5,425,717 A | 6/1995 | Mohiuddin |
| 5,429,596 A | 7/1995 | Arias et al. |
| 5,449,351 A | 9/1995 | Zohmann |
| 5,470,318 A | 11/1995 | Griffith, III et al. |
| 5,480,389 A | 1/1996 | McWha et al. |
| 5,490,845 A | 2/1996 | Racz |
| 5,512,045 A | 4/1996 | Gurchumelidze |
| 5,512,052 A | 4/1996 | Jesch |
| 5,520,652 A | 5/1996 | Peterson |
| 5,542,918 A | 8/1996 | Atkinson |
| 5,569,178 A | 10/1996 | Henley |
| 5,573,519 A | 11/1996 | Zohmann |
| 5,584,820 A | 12/1996 | Gurmarnik |
| 5,591,132 A | 1/1997 | Carrie |
| 5,601,583 A | 2/1997 | Donahue et al. |
| 5,611,778 A | 3/1997 | Brinon |
| 5,628,734 A | 5/1997 | Hatfalvi |
| 5,630,802 A | 5/1997 | Moellmann et al. |
| 5,630,939 A | 5/1997 | Bulard et al. |
| 5,637,096 A | 6/1997 | Yoon |
| 5,669,394 A | 9/1997 | Bergey et al. |
| 5,669,876 A | 9/1997 | Schechter et al. |
| 5,669,882 A | 9/1997 | Pyles |
| 5,672,158 A | 9/1997 | Okada et al. |
| 5,685,852 A | 11/1997 | Turkel et al. |
| 5,725,504 A | 3/1998 | Collins |
| 5,730,754 A | 3/1998 | Obenchain |
| 5,752,969 A | 5/1998 | Cunci et al. |
| 5,779,666 A | 7/1998 | Teirstein |
| 5,779,680 A | 7/1998 | Yoon |
| 5,820,588 A | 10/1998 | Howard, III |
| 5,830,188 A | 11/1998 | Abouleish |
| 5,833,662 A | 11/1998 | Stevens |
| 5,836,914 A | 11/1998 | Houghton |
| 5,836,916 A | 11/1998 | Corn |
| 5,846,226 A | 12/1998 | Urmey |
| 5,853,391 A | 12/1998 | Bell |
| 5,857,996 A | 1/1999 | Snoke |
| 5,871,470 A | 2/1999 | McWha |
| 5,885,217 A | 3/1999 | Gisselberg et al. |
| 5,899,891 A | 5/1999 | Racz |
| 5,913,857 A | 6/1999 | Ritchart et al. |
| 5,921,956 A | 7/1999 | Grinberg et al. |
| 5,941,853 A | 8/1999 | Collins |
| 5,957,881 A | 9/1999 | Peters et al. |
| 5,976,110 A | 11/1999 | Greengrass et al. |
| 6,004,293 A | 12/1999 | Bell |
| 6,039,748 A | 3/2000 | Savage et al. |
| 6,068,642 A | 5/2000 | Johnson et al. |
| 6,095,149 A | 8/2000 | Sharkey et al. |
| 6,113,569 A | 9/2000 | Becker |
| 6,179,828 B1 | 1/2001 | Mottola et al. |
| 6,183,254 B1 | 2/2001 | Cohen |
| 6,190,370 B1 | 2/2001 | Tsui |
| 6,193,704 B1 | 2/2001 | Winters |
| 6,221,048 B1 | 4/2001 | Phelps |
| 6,224,630 B1 | 5/2001 | Bao et al. |

(56) References Cited

U.S. PATENT DOCUMENTS

| | | |
|---|---|---|
| 6,245,044 B1 | 6/2001 | Daw et al. |
| 6,258,111 B1 | 7/2001 | Ross et al. |
| 6,270,703 B1 | 8/2001 | Wildman et al. |
| 6,273,873 B1 | 8/2001 | Fleischer |
| 6,296,624 B1 | 10/2001 | Gerber et al. |
| 6,298,256 B1 | 10/2001 | Meyer |
| 6,363,273 B1 | 3/2002 | Mastrorio et al. |
| 6,371,943 B1 | 4/2002 | Racz et al. |
| 6,558,353 B2 | 5/2003 | Zohmann |
| 6,572,593 B1 | 6/2003 | Daum |
| 6,592,559 B1 | 7/2003 | Pakter et al. |
| 6,610,066 B2 | 8/2003 | Dinger et al. |
| 6,620,180 B1 | 9/2003 | Bays et al. |
| 6,638,238 B1 | 10/2003 | Weber et al. |
| 6,641,563 B1 | 11/2003 | Vitullo et al. |
| 6,708,489 B2 | 3/2004 | Massey et al. |
| 6,709,418 B1 | 3/2004 | Aboul Hosn et al. |
| 6,712,773 B1 | 3/2004 | Viola |
| 6,764,491 B2 | 7/2004 | Frey et al. |
| 6,872,199 B2 | 3/2005 | Cucin |
| 6,899,712 B2 | 5/2005 | Moutafis et al. |
| 6,923,813 B2 | 8/2005 | Phillips et al. |
| 6,925,333 B2 | 8/2005 | Krebs |
| 6,979,317 B2 | 12/2005 | Galt et al. |
| 7,022,109 B1 | 4/2006 | Ditto |
| 7,120,487 B2 | 10/2006 | Nelson |
| 7,181,289 B2 | 2/2007 | Pflueger et al. |
| 7,234,468 B2 | 6/2007 | Johnson et al. |
| 7,244,263 B2 | 7/2007 | Robison et al. |
| 7,318,831 B2 | 1/2008 | Alvarez et al. |
| 7,400,930 B2 | 7/2008 | Sharkey et al. |
| 7,465,278 B2 | 12/2008 | Cicenas et al. |
| 7,615,037 B2 | 11/2009 | Murray et al. |
| 7,632,294 B2 | 12/2009 | Milbodker et al. |
| 7,647,123 B2 | 1/2010 | Sharkey et al. |
| 7,727,186 B2 | 6/2010 | Makower et al. |
| 7,740,631 B2 | 6/2010 | Bleich et al. |
| 7,806,834 B2 | 10/2010 | Beckman et al. |
| 7,819,819 B2 | 10/2010 | Quick et al. |
| 7,828,748 B2 | 11/2010 | Hibner |
| 7,854,706 B2 | 12/2010 | Hibner |
| 7,909,822 B2 | 3/2011 | Guerra |
| 7,918,804 B2 | 4/2011 | Monson et al. |
| 7,955,057 B2 | 6/2011 | Kuehner et al. |
| 8,016,846 B2 | 9/2011 | McFarlin et al. |
| 8,088,119 B2 | 1/2012 | Saal et al. |
| 8,088,291 B2 | 1/2012 | Hershberger et al. |
| 8,100,874 B1 | 1/2012 | Jordan |
| 8,277,393 B2 | 10/2012 | Miller et al. |
| 8,277,437 B2 | 10/2012 | Saal et al. |
| 8,292,909 B1 | 10/2012 | DuBois et al. |
| 8,298,254 B2 | 10/2012 | Dubois et al. |
| 8,308,746 B2 | 11/2012 | Pravong et al. |
| 8,366,694 B1 | 2/2013 | Jordan et al. |
| 8,414,587 B2 | 4/2013 | Saal et al. |
| 8,657,842 B2 | 2/2014 | DuBois et al. |
| 8,685,052 B2 | 4/2014 | DuBois et al. |
| 8,815,099 B1 | 8/2014 | DuBois et al. |
| 8,840,632 B2 | 9/2014 | DuBois et al. |
| 8,882,793 B2 | 11/2014 | DuBois et al. |
| 9,532,796 B2 | 1/2017 | DuBois et al. |
| 2002/0183758 A1 | 12/2002 | Middleton et al. |
| 2003/0130577 A1 | 7/2003 | Purdy et al. |
| 2003/0176778 A1 | 9/2003 | Messing et al. |
| 2003/0187383 A1 | 10/2003 | Weber et al. |
| 2003/0212395 A1 | 11/2003 | Woloszko et al. |
| 2003/0236549 A1 | 12/2003 | Bonadio et al. |
| 2004/0034339 A1 | 2/2004 | Stoller et al. |
| 2004/0049217 A1 | 3/2004 | Ross et al. |
| 2004/0064127 A1 | 4/2004 | Lerner |
| 2004/0092992 A1 | 5/2004 | Adams et al. |
| 2004/0098006 A1 | 5/2004 | Nakanishi |
| 2004/0102760 A1 | 5/2004 | Hsue et al. |
| 2004/0127963 A1 | 7/2004 | Uchida et al. |
| 2004/0210231 A1 | 10/2004 | Boucher et al. |
| 2004/0267282 A1 | 12/2004 | Shkarubo et al. |
| 2005/0004563 A1 | 1/2005 | Racz et al. |
| 2005/0010205 A1 | 1/2005 | Hovda et al. |
| 2005/0090801 A1 | 4/2005 | Racz et al. |
| 2005/0197661 A1 | 9/2005 | Carrison et al. |
| 2005/0203527 A1 | 9/2005 | Carrison et al. |
| 2005/0234425 A1 | 10/2005 | Miller et al. |
| 2005/0261692 A1 | 11/2005 | Carrison et al. |
| 2006/0004369 A1 | 1/2006 | Patel et al. |
| 2006/0064101 A1 | 3/2006 | Arramon |
| 2006/0110017 A1 | 5/2006 | Tsai et al. |
| 2006/0111728 A1 | 5/2006 | Abdou |
| 2006/0129062 A1 | 6/2006 | Nicoson et al. |
| 2006/0229550 A1 | 10/2006 | Staid et al. |
| 2006/0239982 A1 | 10/2006 | Simpson |
| 2006/0258951 A1 | 11/2006 | Bleich et al. |
| 2006/0259060 A1 | 11/2006 | Whitson et al. |
| 2006/0264994 A1 | 11/2006 | Schomer et al. |
| 2006/0271196 A1 | 11/2006 | Saal et al. |
| 2006/0271197 A1 | 11/2006 | Saal et al. |
| 2006/0284994 A1 | 12/2006 | Kim |
| 2007/0055259 A1 | 3/2007 | Norton et al. |
| 2007/0135768 A1 | 6/2007 | Carlsen |
| 2007/0142842 A1 | 6/2007 | Krueger et al. |
| 2007/0149895 A1 | 6/2007 | McCullough et al. |
| 2007/0162062 A1 | 7/2007 | Norton et al. |
| 2008/0183175 A1 | 7/2008 | Saal et al. |
| 2008/0183192 A1 | 7/2008 | Saal et al. |
| 2008/0188826 A1 | 8/2008 | Saal |
| 2008/0188827 A1 | 8/2008 | Saal |
| 2008/0214955 A1 | 9/2008 | Speeg et al. |
| 2008/0221586 A1 | 9/2008 | Garcia-Bengochea et al. |
| 2008/0221589 A1 | 9/2008 | Balling et al. |
| 2008/0221605 A1 | 9/2008 | Saal et al. |
| 2008/0249553 A1* | 10/2008 | Gruber ............ A61B 17/32002 606/171 |
| 2008/0255563 A1 | 10/2008 | Farr et al. |
| 2008/0294166 A1 | 11/2008 | Goldin et al. |
| 2008/0294167 A1 | 11/2008 | Schumacher et al. |
| 2008/0319341 A1 | 12/2008 | Taylor et al. |
| 2009/0048678 A1 | 2/2009 | Saal et al. |
| 2009/0076486 A1 | 3/2009 | Cucin |
| 2009/0105609 A1 | 4/2009 | Thompson et al. |
| 2009/0216234 A1 | 8/2009 | Farr et al. |
| 2009/0259126 A1 | 10/2009 | Saal et al. |
| 2009/0270896 A1 | 10/2009 | Sullivan et al. |
| 2010/0063416 A1 | 3/2010 | Cicenas et al. |
| 2010/0152611 A1 | 6/2010 | Parihar et al. |
| 2010/0179528 A1* | 7/2010 | Shadduck .......... A61B 17/3203 606/27 |
| 2010/0211083 A1 | 8/2010 | Sauer |
| 2010/0297577 A1 | 11/2010 | Cohen |
| 2011/0028898 A1* | 2/2011 | Clark, III ........... A61B 18/1477 604/151 |
| 2011/0054349 A1 | 3/2011 | Hibner |
| 2011/0098596 A1 | 4/2011 | Ozturk et al. |
| 2011/0160731 A1 | 6/2011 | Bleich et al. |
| 2011/0196286 A1* | 8/2011 | Robertson ...... A61B 17/320068 604/22 |
| 2011/0306879 A1 | 12/2011 | Saal et al. |
| 2011/0313433 A1 | 12/2011 | Woodard, Jr. et al. |
| 2012/0283742 A1 | 11/2012 | Dubois et al. |
| 2013/0046199 A1 | 2/2013 | DuBois et al. |
| 2013/0211321 A1 | 8/2013 | DuBois et al. |
| 2013/0211438 A1 | 8/2013 | DuBois et al. |
| 2014/0081266 A1 | 3/2014 | DuBois et al. |
| 2015/0150580 A1 | 6/2015 | DuBois et al. |
| 2015/0201995 A1 | 7/2015 | DuBois et al. |

FOREIGN PATENT DOCUMENTS

| | | |
|---|---|---|
| GB | 529 800 | 11/1940 |
| RU | 2029533 | 2/1995 |
| WO | WO 93/14700 | 8/1993 |
| WO | WO 97/26835 | 7/1997 |
| WO | WO 2006/027549 | 3/2006 |
| WO | WO 2006/119455 | 11/2006 |
| WO | WO 2008/094436 | 8/2008 |

(56) References Cited

FOREIGN PATENT DOCUMENTS

| | | |
|---|---|---|
| WO | WO 2008/094444 | 8/2008 |
| WO | WO 2008/094439 | 9/2008 |
| WO | WO 2008/095177 | 10/2008 |
| WO | WO 2009/052194 | 4/2009 |
| WO | WO 2009/124192 | 10/2009 |
| WO | WO 2012/003383 | 1/2012 |
| WO | WO 2013/119336 | 8/2013 |
| WO | WO 2014/028046 | 2/2014 |

OTHER PUBLICATIONS

U.S. Appl. No. 11/838,692, filed Aug. 14, 2007.
U.S. Appl. No. 13/213,016, filed Aug. 18, 2011.
U.S. Appl. No. 12/417,165, filed Apr. 2, 2009.
U.S. Appl. No. 11/848,565, filed Aug. 31, 2007.
U.S. Appl. No. 11/848,564, filed Aug. 31, 2007.
U.S. Appl. No. 11/848,562, filed Aug. 31, 2007.
U.S. Appl. No, 13/174,416, filed Jun. 30, 2011.
U.S. Appl. No. 13/657,773, filed Oct. 22, 2012.
U.S. Appl. No. 13/734,878, filed Jan. 4, 2013.
U.S. Appl. No. 13/941,267, filed Jul. 12, 2013.
U.S. Appl. No, 13/735,915, filed Jan. 7, 2013.

* cited by examiner

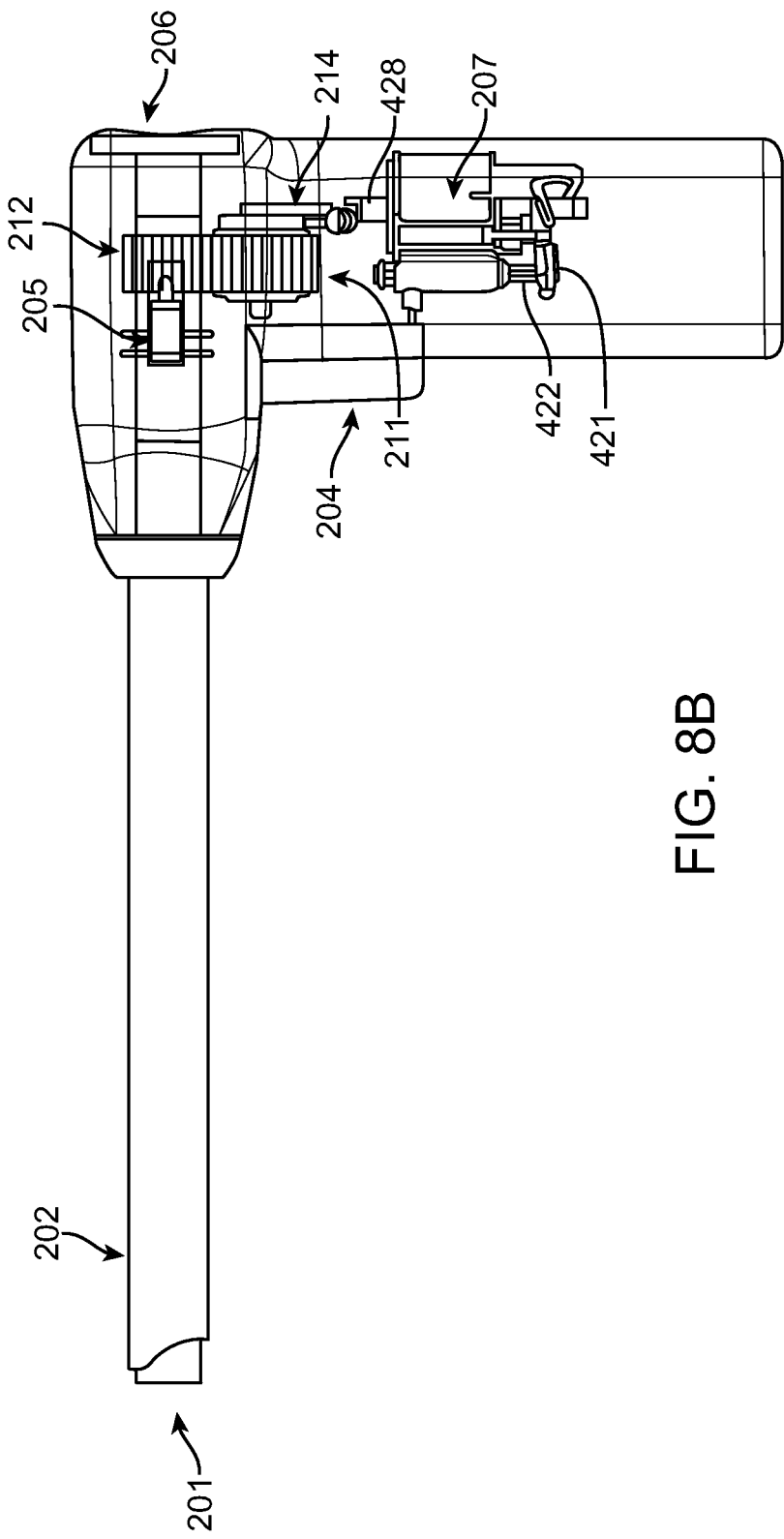

VACUUM POWERED ROTARY DEVICES AND METHODS

CROSS-REFERENCE TO RELATED APPLICATIONS

This application claims the benefit of priority to U.S. Provisional Patent Application No. 61/597,648 filed Feb. 10, 2012 and U.S. Provisional Patent Application No. 61/684,656 filed Aug. 17, 2012, the contents of which are incorporated herein by reference in their entirety.

FIELD OF THE INVENTION

The present devices and methods relate generally to medical devices and methods for performing work on tissue in various regions of a patient's body, including, for example, vacuum powered devices having a rotational output.

BACKGROUND

Hand-held powered medical devices typically receive power from external sources such as receiving mechanical power through a rotating cable, electric power via conductive cables, or compressed air via tubing. Batteries may also be integrated into a medical device to provide power to the device.

Hand-held powered medical devices that have sources of power commonly require consoles that connect to the hand-held portion of the device. The power consoles require capital investment, storage, service, and suffer from obsolescence as technology changes.

When an electric motor is used to provide rotational motion to a cutting device, the additional weight of the electric motor may cause operator fatigue. Wires from an external power supply are inconvenient to make the connections and to have the wires attached to the device during use.

Electric motors increase the cost of a device because of the increased cost of the motor in addition to the cost of a power supply (in the case of an externally powered motor) or the cost of a recharging unit (when rechargeable batteries are used). The addition of electric motors makes sterilization of the device more difficult and adds mass to the device. The presence of batteries adds potentially toxic chemicals that present additional challenges related to toxicity hazards in addition to sterilization difficulties. Also, medical devices that include electric motors are usually made to be re-usable which requires a system for reprocessing the device.

Additionally, bleeding may commonly occur during surgical procedures when tissue is cut. Bleeding may obscure the surgical field and cause loss of blood. Bleeding that does not stop by bodily coagulation processes must be stopped through interventional measures.

Thus, there is a need for more efficient, safer and cost effective devices and methods for performing work on tissue, e.g., cutting, resecting, morcellating, excising and/or removing tissue, in various regions of the body.

BRIEF SUMMARY

The present devices and methods relate generally to vacuum or suction powered medical devices and methods for performing work on tissue, e.g., cutting, resecting, excising, morcellating and/or evacuating tissue from various regions of a patient's body. In certain variations, the devices may produce a rotational motion by converting a linear reciprocating motion to a rotational motion, causing a cutting shaft or tube or other tool or operable element of the device to rotate to perform work on a tissue in various regions of the body. In certain variations, the devices may include electrocautery or ablation components or features.

In certain variation, a medical device is provided which may include a mechanism powered by suction created by a vacuum source, where the mechanism is configured to produce a linear reciprocating motion. A component coupled to the mechanism or the mechanism may convert the linear reciprocating motion to a rotary motion. A working end may include an operable element where the operable element is coupled to the component such that the rotary motion rotates the operable element.

In certain variations, a medical device or morcellator for cutting tissue from the human body may include a shaft having a proximal end, a distal end, and a lumen extending there between. The shaft may have an opening at the distal end and a sharpened edge surrounding at least a portion of a perimeter of the opening, where the shaft is rotatable about a central axis of the shaft. The device may include a mechanism powered by suction from a vacuum source, where the mechanism produces a linear reciprocating motion. The mechanism and/or a component coupled to the mechanism and coupled to the shaft may convert the linear reciprocating motion to rotary motion, thereby causing the shaft to rotate to cut tissue.

In certain variations, a method for removing tissue from the human body may include one or more of the following steps: advancing a cutting device next to a target tissue; advancing a grasping tool through a lumen of the cutting device and grasping the target tissue; retracting the target tissue proximally to appose, oppose or position the target tissue against a cutting surface of the cutting device; powering the cutting device with suction created by a vacuum source such that the cutting device produces a rotary motion which causes the cutting surface to rotate; cutting tissue with the rotating cutting, surface; and removing the tissue by withdrawing it through the lumen in the cutting device using the grasping tool or evacuating the tissue through the lumen with suction.

In certain variations, a method for performing work on tissue in the human body may include one or more of the following steps: positioning an operable element located on a distal end of a medical device against a target tissue; powering the medical device with suction created by a vacuum source such that the medical device produces a rotary motion which causes the operable element to rotate whereby the operable element performs work on the target tissue, in other variations, a method of powering a medical device may include one or more of the following steps: providing suction created by a vacuum source to the medical device; applying the suction to both sides of a piston within the medical device in an alternating manner to cause the piston to reciprocate in a linear manner, wherein the piston is reciprocated solely by the applied suction; and converting the linear reciprocating motion into a rotary motion, which causes a shaft or tool of the medical device to rotate whereby the tool may perform work on a target tissue.

In certain variations, a method for preventing a vacuum powered mechanism from stalling may include one or more of the following steps: coupling a linear reciprocating drive piston of the vacuum powered mechanism to a cam or crank wheel and a cam follower; and exerting a force on a crank wheel or cam surface with a cam follower, thereby causing the crank wheel or cam surface to translate into a position wherein the vacuum powered mechanism is unlikely to stall or does not stall when the drive piston reverses direction. In certain variations, a method for removing tissue from the human body may include one or more of the following steps: advancing a cutting device next to a target tissue; positioning the target tissue against a cutting surface of the cutting device; providing an oscillating rotary motion to cause oscillating rotary motion of the cutting surface; cutting tissue with the oscillating rotary cutting surface; and avoiding or preventing excessive twisting of the tissue as the tissue is cut or withdrawn through a lumen of the cutting device by cutting the tissue with the oscillating rotary cutting surface.

BRIEF DESCRIPTION OF THE SEVERAL VIEWS OF THE DRAWINGS

FIGS. 8A-8C illustrate a variation of a medical device having a rotating, cutting tube or shaft where the device is powered by a vacuum powered mechanism.

DETAILED DESCRIPTION

Figure 1:
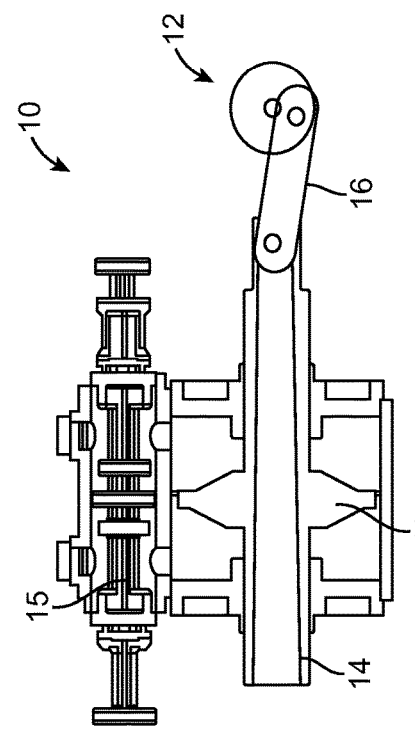
FIGS. 1-4 show cross sections of a variation of a vacuum or suction powered mechanism coupled to a component for converting linear reciprocating motion to rotational motion, including a crank mechanism.

Variations of the devices are best understood from the detailed description when read in conjunction with the accompanying drawings. It is emphasized that, according to common practice, the various features of the drawings may not be to-scale. On the contrary, the dimensions of the various features may be arbitrarily expanded or reduced for clarity. The drawings are taken for illustrative purposes only and are not intended to define or limit the scope of the claims to that which is shown.

Various suction or vacuum powered medical devices and methods for utilizing such devices are described herein. Various vacuum or suction powered mechanisms and components for such medical devices are described herein which may generate motion, e.g., linear and/or rotational motion, for actuating or operating tools, cutters or end effectors or operable elements which are located on, connected to, coupled to or otherwise associated with the medical devices. Any of the vacuum or suction powered mechanisms or motors described in the U.S. patent application Ser. No. 13/734,878 and filed on Jan. 4, 2013 or U.S. patent application Ser. Nos. 13/657,773, 13/550,407 or 13/174,416 may also be utilized in any of the medical devices described herein. The medical devices may be used to perform a variety of procedures, e.g., tissue cutting, morcellating, grinding, drilling, and or resection procedures in various regions throughout the body, including the nasal cavity, the uterus, abdomen and thoracic cavity and to perform any procedures described in the above referenced patent applications or US patent application No. 61/597,642. The devices may be used in general surgery and/or minimally invasive surgery, e.g., laparoscopy or thoracoscopy procedures. The contents of U.S. patent application Ser. No. 13/734,878 and filed on Jan. 4, 2013, U.S. patent application Ser. Nos. 13/657,773, 13/550,407, 13/174,416 and 61/597,642 are hereby incorporated by reference in their entirety.

In certain variations, a medical device may include a mechanism or motor configured to be powered by suction created by a vacuum or suction source. The mechanism may produce a linear reciprocating motion or output. The linear reciprocating motion may be converted or translated to a rotary motion or output. For example, the mechanism may include or be coupled to a component where the component can convert linear reciprocating motion generated by the mechanism to a rotary motion or rotary output. The medical device may also include a working end having an operable element. The mechanism and/or component may be connected to or coupled to the working end or other portion of the device, e.g., a shaft, output shaft, operable element or other extension, such that the rotary motion produced by the component causes the working end, shaft, output shaft, operable element and/or other extension to rotate to affect or perform work on tissue, e.g., to cut, resect or excise tissue. In certain variations, the medical device may be powered solely by suction or vacuum from a vacuum source.

In one variation, a medical device or morcellator may include a mechanism and an output shaft coupled to the mechanism for performing an intended function of the medical device, e.g., cutting or drilling tissue. The medical device may be connected to a vacuum source or a source of suction which provides power to the mechanism or motor. The mechanism or motor may produce a linear output or linear reciprocating motion which may be converted to an oscillating rotating or rotary output or motion. For example, a drive piston of the mechanism may by connected or coupled to a rack. Linear reciprocating motion of the drive piston may cause the rack to reciprocate linearly back and forth. The rack may engage and drive a pinion gear located on or in the device, where the linear reciprocating, back and forth motion of the rack causes the pinion gear to rotate in alternating clockwise and counterclockwise directions, thereby generating or producing an oscillating rotating or rotary motion or converting the linear reciprocating motion into oscillating rotating or rotary motion. The hack and forth or oscillating rotating or rotary motion of the pinion gear causes a back and forth or oscillating rotating or rotary motion of an output shaft of the medical device which may be coupled to the mechanism and/or rack and pinion gear. Optionally, the linear reciprocating motion may be converted to a continuous rotating or rotary output or motion.

In certain variations, the linear output or linear reciprocating motion of a vacuum or suction powered mechanism may be converted to a rotating or rotary motion or output (e.g., continuous, interrupted or oscillating, rotating, or rotary motion) using various types of components. For example, linear motion may be converted to rotating or rotary motion through a crank mechanism, a rack and pinion gear mechanism, a pivoting rack and pinion gear mechanism, a ratchet mechanism (e.g., a rack and pinion with a spring ratchet mechanism), a two sided rack drive mechanism (described in more detail below) or any other component or mechanism known to persons having ordinary skill in the art and suitable for converting linear motion to rotating or rotary motion. The created rotational motion may cause rotational motion of an output shaft, working end, operable element, or tool of a medical device to perform work on various tissues.

In certain variations, a component of a vacuum powered medical device used to convert linear to rotary motion may include a cam or crank wheel and a cam follower. The cam follower may exert a force on the crank wheel or cam surface to cause the crank wheel or cam surface to rotate and translate into a position where the vacuum powered mechanism is unlikely to stall.

In certain variations, a vacuum powered mechanism for use in any of the devices and mechanism/component arrangements described herein may include a drive shaft or drive piston located in a chamber. The suction may be applied to both sides of a drive shaft or drive piston in an alternating, manner to cause the drive shaft or drive piston to reciprocate between a drive stroke and a return stroke to create a reciprocating motion. The mechanism may include a shuttle body or valve coupled to the drive shaft by a linkage. The shuttle body or valve may be moveable between a forward and return position, where movement between the forward and return positions alternates a fluid path between the chamber and vacuum source so that during application of suction or vacuum from the vacuum source movement of the Shuttle body or valve causes the drive shaft to cycle between the drive stroke and the return stroke.

The linkage may couple the drive shaft to the shuttle body or valve such that as the drive shaft approaches the end of the drive or return stroke the linkage transfers a force to the Shuttle body or valve to assist in switching, between the forward and return positions and prevents or minimizes unstable flutter of the shuttle body or valve between the forward and return positions.

In certain variations, a vacuum or suction powered medical device for cuffing tissue from the human body may include an output shaft, e.g., an elongate cutting shaft or elongate cutting tube. The shaft may include a proximal end, a distal end, and a lumen extending between the proximal and distal ends. The shaft may include an opening at the distal end and a sharpened edge may surround at least a portion of a perimeter of the opening. The shaft may be rotatable about a central axis of the shaft. The medical device may include a mechanism powered by suction from a vacuum source. The mechanism may produce a linear reciprocating motion. The mechanism may be coupled to or include a component and the component may be coupled to the shaft. The component may convert the linear reciprocating motion to rotary motion and the rotary motion may cause the shaft to rotate to cut tissue.

A grasper may be advanced distally through the shaft lumen, and the grasper may draw or retract tissue proximally against the sharpened distal edge or extremity of the shaft to allow for cutting or excision of the tissue, e.g., as the sharpened distal edge or extremity of the shaft rotates. The cut tissue may be removed or evacuated through the shaft lumen and out of the body.

In certain variations, an output shaft such as an elongate cutting tube or shaft may optionally be positioned within an exterior sheath or exterior shaft. The exterior sheath or shaft may be coupled to or extend from a chamber, where a mechanism and/or component (as described herein) may be positioned in the chamber and coupled to the elongate cutting shaft or tube. The output shaft or elongate cutting shaft or tube may include a lumen for accessing target tissue, for example, with a tenaculum, grasper or other surgical instrument which may be advanced through the lumen and out of an opening located at the distal end of the cutting shaft or tube. The opening may be in fluid communication with the lumen.

Tissue may be evacuated, or removed from the body through the lumen of the cutting shaft or tube.

The cutting shaft or tube may have a sharpened edge surrounding, at least a portion of the perimeter of the opening. The cutting shaft or tube may be driven or rotated in either an oscillating rotating or fully rotational manner (continuous or interrupted) via a mechanism which produces linear motion, which is converted to rotational motion, e.g., via a component coupled to the mechanism. The component for converting linear to rotational motion is included in or coupled to the mechanism and the cutting shaft or tube to rotate the cutting shaft or tube as described herein. The rotating cutting shaft or tube may be used to morcellate tissue, break up or remove tissue clumps, or cut or resect tissue in various regions of the body, e.g., in the uterus, abdomen or thoracic cavity (during general surgery or laparoscopic or thoracoscopic procedures) or the nasal cavity. The morcellated or cut tissue may be extracted from the body through the lumen of the cutting shaft or tube or through a port for collection and/or removal.

In another variation, an output shaft of a vacuum or suction powered medical device may include a collet or socket to assemble or attach a drill bit, grinding wheel, rotating cutting blade, or burr on the tip or distal end of the output shaft, for drilling or cutting into tissue, e.g., hard tissue such as bone. Various end effectors for performing work on tissue, soft tissue or hard tissue, may be coupled to the output shaft via the collet or other fastener. Alternatively, an end effector, e.g., a drill bit or burr, may be permanently affixed to the shaft of the device. The output shaft may be driven in either an oscillating rotating or fully rotational manner as described herein.

In certain variations, an operator or user may connect a cutting device powered by suction or vacuum to a vacuum source. The device may include an output shaft, e.g., the output shaft may be in the form of a cutting tube having a lumen extending therethrough and an opening, at its distal end. The distal end of the cutting tube may include a sharpened cutting surface, e.g., on at least a portion of the perimeter of the opening. The cutting tube may be inserted into a body and advanced to a target tissue site. The operator may then advance a grasping device, e.g., a tenaculum, through the lumen of the cutting tube and through the distal opening. The grasping device may be used to pull tissue against the sharpened cutting surface on the distal end of the cutting tube. A control may be actuated which causes a mechanism or motor powered by suction or solely by suction to cause rotating of the cutting tube either in full rotary motion or oscillating rotary motion, thereby cutting the tissue pulled against the sharpened cutting surface of the cutting tube. The mechanism may produce reciprocating linear motion that is converted into rotational motion to cause the cutting tube, coupled thereto, to rotate (as described herein). Optionally, the mechanism may start moving as soon as the vacuum source is connected to the device. As the tissue is cut, the grasping device may retract or remove the cut portion of tissue proximally through the lumen of the cutting tube. Optionally, the cut tissue may be evacuated through a lumen of the cutting tube using suction from the same or different vacuum source used to operate or motivate the mechanism of the device. Optionally, the output shaft may be coupled to a cutting tool or other operable element to cut or perform work on tissue.

In another variation, an operator or user may connect a device powered by suction to a vacuum source. The device may include an output shaft with a tool, such as a drill bit, cutting wheel, burr, or grinding wheel, coupled to the distal end of the output shaft. The output shaft may be inserted into a body and advanced to a target tissue site. A control may be actuated which causes a mechanism or motor powered by suction or vacuum or solely by suction or vacuum to rotate the output shaft either in full or complete rotary motion or oscillating rotary motion, thereby causing a tool to perform work on tissue. For example, the tool may morcellate, cut, drill, scrape, or grind the tissue, e.g., break up, cut or remove tissue or tissue pieces. The mechanism may produce reciprocating linear motion that is converted into rotational motion to cause the tool, coupled thereto, to rotate (as described herein). Optionally, the mechanism may start moving as soon as the vacuum source is connected to the device. Optionally, the cut or morcellated tissue may be evacuated through a lumen of the output shaft or medical device or removed with a grasping tool.

The various medical devices described herein are configured to be connected to a source of suction or vacuum, which provides power, (e.g., the vacuum source may be the sole source of power or motion), for a mechanism or motor to actuate an operable element, a tool or shaft for performing work on tissue in the human body. In certain variations, the medical device may include a shaft having two or more conductors or electrodes to carry bipolar electrical energy to conductor or electrode termination points where conductors are exposed at the distal extremity or other portion of the device shaft. When the bipolar energy is activated, bipolar energy flows between the conductors or electrodes whereby the energy may be used to cauterize or ablate tissue.

In another variation, a medical device may include a shaft having one or more conductors or electrodes to carry monopolar electrical energy to a conductor or electrode termination point where a conductor or electrode is exposed at the distal extremity or other portion of the device shaft. When the monopolar energy is activated, energy flows between the conductor or electrode and a grounding pad (positioned at a remote location on the patients' body) whereby the energy may be used to cauterize or ablate tissue.

In another variation, a medical device may include a shaft having one or more conductors or electrodes to carry electrical energy to a termination point where one or more resistors are exposed at the distal extremity or other portion of the device shaft. Electrical energy flowing through the resistor causes it to become hot or causes its temperature to rise and to thereby cauterize or ablate tissue.

In certain variations, malleable wires may be positioned within the shaft or device which provide the shaft or device with malleable characteristics and which allow the device or shaft to be manipulated or reshaped in order to access certain regions of the body. Optionally, at least a portion of these malleable wires may also serve as conductors or electrodes for cauterizing or ablating tissue.

Optionally, a medical device may include any of the cauterizing or ablation features described supra where the device is with or without a mechanical cutter or tool, and the device is configured to cauterize, ablate or perform electrosurgical cutting of tissue.

Any of the cauterizing or ablation features described herein may be utilized with the devices or methods described herein and the devices or methods described in the above referenced patent applications.

Any of the devices described herein may be handheld. The source of vacuum or suction for use with the devices described herein may be an external or internal source. The length or width of the medical devices or shafts of such devices may be sufficient for accessing, various regions of the body, and/or may be adjustable, e.g., the shaft may have a length sufficient for accessing the nasal cavity or a length sufficient for accessing the uterine space via the vagina and cervix or for accessing the abdomen or thoracic cavity, e.g., via minimally invasive procedures.

In certain variations, the devices described herein may be used as a part of a bigger or more involved surgery or procedure, e.g., where the device is used to cut up, break up, morcellate, and/or remove tissue pieces or clumps from within the body, e.g., tissue pieces or clumps already worked on, affected or surgically prepared, e.g., tissue scraped or cut from a uterine or other wall.

As described supra, the devices and methods described herein provide a number of advantages. The devices and methods may combine and provide all of the functions required to perform work on tissue without the need for power consoles, without the need for an unmanageable number of devices or multiple devices. The devices may be powered using only a source of suction or vacuum, therefore, no additional external or internal power sources, e.g., a pressurized air source, may be required.

Certain devices described herein may be powered solely by a source of suction making them very low in cost, easy to set up, and their disposability allows technology improvements to be implemented seamlessly without concerns for compatibility with installed capital equipment. Optionally, the devices may be powered with a source of suction in combination with another power source.

The devices and methods described herein may include electrocautery or ablation features. The electrocautery or ablation features may be integrated into the device at the distal extremity of the shaft or anywhere along a shaft or other extension of the medical device, e.g., close to a cutting window or opening on a shaft, where tissue bleeding may occur as a result of cutting or morcellating tissue. As a result, any bleeding may be addressed immediately upon identification without the need to exchange the cutting device with a separate coagulation device. This saves time, prevents blood loss, reduces the likelihood that blood will obscure the operative field, and saves the expense of additional coagulation devices.

Exemplary Suction or Vacuum Powered Mechanisms and/or Components for Converting Linear Motion to Rotary Motion As stated supra, any of the mechanisms and/or components described herein or in the above referenced patent applications may be utilized to operate and/or create linear reciprocating and/or rotational motion for any of the medical deices described herein.

FIGS. 1-4 show one variation of a mechanism powered by suction from a vacuum or suction source, where the mechanism is coupled to or includes a component for converting linear reciprocating motion to rotating or rotary motion and may be utilized for operating a medical device. The mechanism 10 may include a shuttle body 15 and a drive piston 11 and a drive piston shaft 14 connected to or integrated with the drive piston 11. The drive piston 11 or drive piston shaft 14 may be coupled or connected to a crank arm 16 of a crank mechanism 12. Optionally, the drive piston 11 or drive piston shaft 14 may be coupled to an output shaft which is connected to or coupled to a crank arm 16 of a crank mechanism 12. The crank mechanism 12 may be coupled to a rotational output shaft or other tool to rotate or actuate the shaft or tool to perform work on a tissue.

Suction created by the vacuum or suction source causes the drive piston 11 and drive piston shaft 14 to reciprocate linearly, back and forth. The back and forth linear reciprocation of the drive piston 11 and drive piston shaft 14 of the mechanism 10 is transferred to the crank area 16 which drives the crank mechanism 12 in a clockwise or counter-clockwise direction, thereby generating or producing a rotary output motion or converting the linear reciprocation motion into rotary motion. Optionally, the drive piston 11 and drive piston shaft 14 may cause an output shaft or other connector to reciprocate linearly back and forth which in turn drives the crank mechanism 12.

FIGS. 1 through 4 taken together illustrate this conversion of linear reciprocating motion to rotary motion. The suction powered mechanism 10 is shown, where the mechanism 10 is driving the crank mechanism 12 in a clockwise direction to create rotary motion.

FIG. 1 shows the suction powered mechanism 10 driving the crank mechanism 12 in a clockwise direction, where the crank mechanism is at about the 1:00 position.

Figure 2:
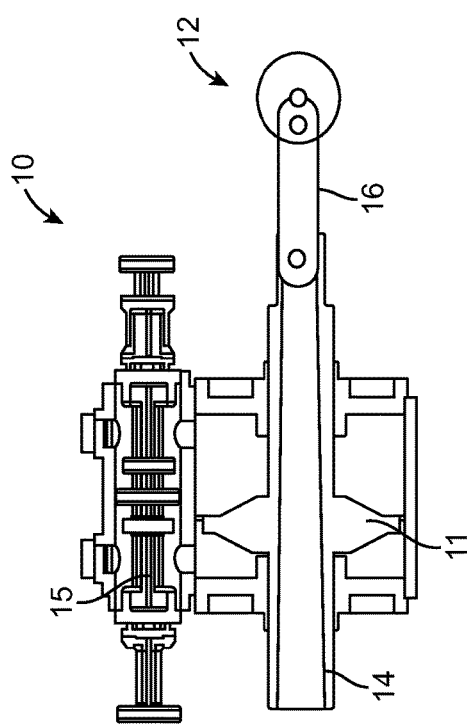

FIG. 2 shows the suction powered mechanism 10 driving the crank mechanism 12 in a clockwise direction, where the crank mechanism is at about the 3:00 position.

Figure 3:
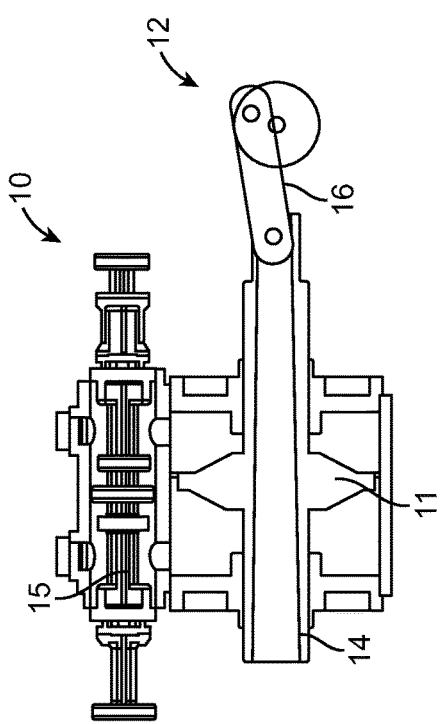

FIG. 3 shows the suction powered mechanism 10 driving a crank mechanism 12 in a clockwise direction, where the crank mechanism is at about the 6:30 position.

Figure 4:
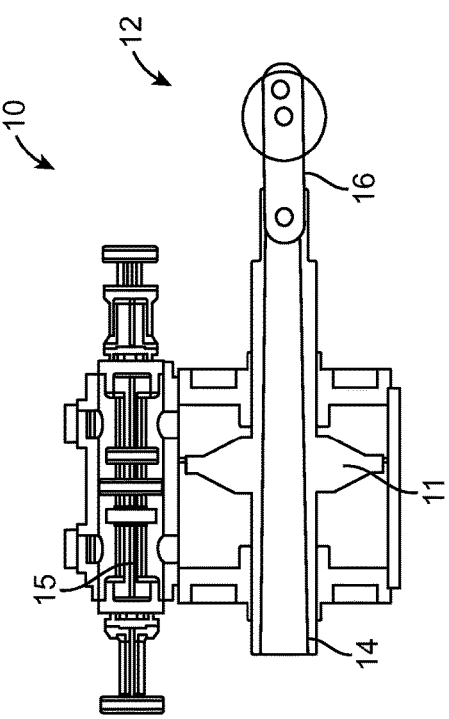

FIG. 4 shows the suction powered mechanism 10 driving a crank mechanism 12 in a clockwise direction, where the crank mechanism is at the 9:00 position, moving toward a complete revolution in the clockwise direction. The produced rotary or rotational motion may cause an output shaft or an extension or tool of a device operated by the mechanism 10 to rotate. For example an output shaft which performs work on a tissue or causes a tool to actuate or perform work on tissue may be coupled to the crank mechanism, which causes the output shaft to rotate.

In certain variations, a mechanism and component assembly may optionally include a ratchet mechanism to ensure that an output shaft (attached to the device and/or coupled to the crank mechanism) rotates in the desired direction. Additionally, the ratchet mechanism may include a pawl to cause the crank mechanism or crank arm assembly to become unstable and thereby move past stall locations at, e.g., at about the 9:00 and 3:00 positions of the crank mechanism.

Mechanisms or motors for producing linear reciprocating motion, which are powered by suction from a vacuum source, may reverse direction at the end of their stroke. In certain variations, the mechanisms may stall and stop operating because these vacuum or suction powered mechanisms use pressure from ambient air to cause a drive piston of the mechanism to translate rather than using compressed or pressurized air or steam. Pressurized or compressed air or steam has the advantage of continuing to expand within a cylinder which allows the pressurized or compressed air or steam to push through mechanical "top-dead-center" situations or stall points. In certain mechanisms, flywheels May use spinning mass to transition through stall points; however, flywheels increase the weight of a device and can be difficult to set into motion without a "starting mechanism."

When using a conventional crank mechanism or component with a vacuum powered mechanism there is a possibility that the vacuum powered mechanism will stall when a drive piston or drive shaft of the vacuum powered mechanism reverses direction. This may occur when various components of the vacuum powered mechanism and the crank mechanism, e.g., the piston linkage, linkage arm, crank linkage, and/or the center of rotation on the crank, are aligned (in the "top-dead-center" position). When in this position, the force exerted by the drive piston does not cause rotary motion, rather, the hub at the center of rotation of the crank mechanism exerts an equal and opposite force against the drive piston that results in static equilibrium of the vacuum powered mechanism and the components of the crank mechanism in no rotary motion.

Figure 5:
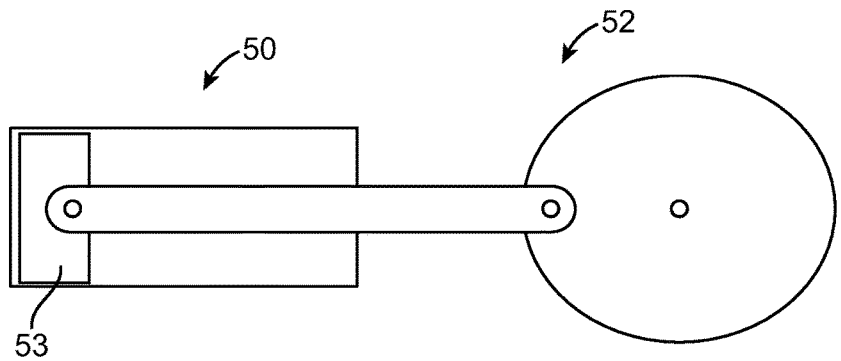
FIG. 5 shows a cross sectional side view of a variation of a vacuum or suction powered mechanism coupled to a crank mechanism.

For example, the suction or vacuum powered mechanism 50 shown in FIG. 5 includes a crank mechanism 52, where the vacuum powered mechanism 50 and crank mechanism 52 are shown in the stalled position. The drive piston 53 of the mechanism 50 is being driven to the right, but the crank mechanism 52 is aligned with the drive piston 53 force, and as a result the vacuum powered mechanism 50 stalls.

FIGS. 6A-6E, show a variation of a component or mechanism for converting linear motion to rotary motion in the form of an anti-stall crank mechanism 114. The anti-stall crank mechanism 114 provides a rotational output that does not stall or that at least minimizes stall. The crank mechanism 114 can overcome top-dead-center situations or stall points when a vacuum powered mechanism for producing linear reciprocating motion reverses direction. The crank mechanism 114 may prevent a vacuum powered mechanism from stalling, which is typically caused by alignment of elements of the vacuum powered mechanism and the component for converting linear motion to rotary motion. Such alignment may takes place when the drive piston of the vacuum powered mechanism reverses direction, and the stalling can cause the rotation to be stopped or halted.

Figure 6A:
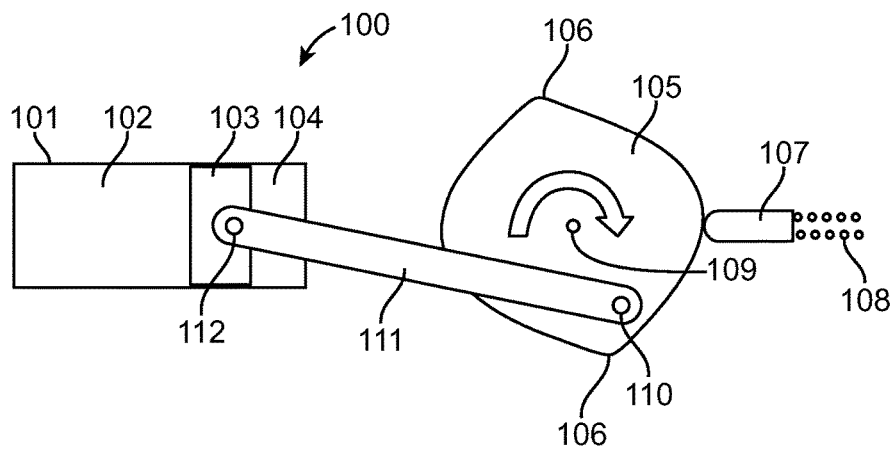
FIGS. 6A-6E illustrate a cross sectional side view of a variation of a vacuum or suction powered mechanism coupled to an anti-stall crank mechanism.

FIG. 6A illustrates a cross sectional side view of a vacuum or suction powered mechanism 100 which includes or is coupled to an anti-stall crank mechanism 114. The vacuum or suction powered mechanism 100 includes a mechanism body 101. A drive piston 103 is located within the mechanism body 101. A proximal vacuum chamber 102 is located to the left (referring to the left side of the drawing in FIGS. 6A-6E) of the drive piston 103. The proximal vacuum chamber 102 is alternately evacuated and filled with ambient pressure air. When the proximal vacuum chamber 102 is evacuated, the drive piston 103 moves in the proximal (leftward) direction within the mechanism body 101. When the proximal vacuum chamber 102 is filled with ambient pressure air, the drive piston 103 moves in the distal (rightward) direction within the mechanism body 101. The drive piston 103 moves toward the chamber that is evacuated and away from the chamber that has ambient air pressure.

A distal vacuum chamber 104 is located to the right (referring to the right side of the drawing in FIGS. 6A-6F) of the drive piston 103. The distal vacuum chamber 104 is alternately evacuated and filled with ambient pressure air. When the distal vacuum chamber104 is evacuated, the drive piston 103 moves in the distal (rightward) direction. When the distal vacuum chamber 104 is filled with ambient pressure air, the drive piston 103 moves in the proximal (leftward) direction.

The drive piston 103 may be connected to the crank arm 111 by the piston linkage 112 and the crank arm 111 may be connected to the cam or crank wheel 105. The crank wheel 105 may be connected to the crank arm 111 by the crank linkage 110 and the crank wheel 105 may be driven in rotary motion by the drive piston 103. The crank wheel 105 rotates about the crank wheel hub 109 and may drive an output shaft or other tool of the device (not shown) in rotary motion. The output shaft or tool may be coupled to the crank wheel 105, crank mechanism 114 or the vacuum powered mechanism 100 such that rotary motion is transferred to the output shaft or tool. The rotary motion of the output shaft allows the output shaft to perform work on tissue or to actuate an operable element or tool coupled to the output shaft or directly to the crank wheel 105 or other portion of the crank mechanism 114.

The cam or crank wheel 105 may include one or more cam lobes or crank lobes 106. The crank lobes 106 may be located along the crank wheel 105, for example, in a location that is a few degrees before the reversal point on the vacuum powered mechanism 100. The crank lobe 106 may maintain contact with a cam follower 107 positioned adjacent the crank wheel 105, thereby compressing the cam follower spring 108.

Force supplied by the cam follower spring 108 forces the cam follower 107 against the crank wheel 105, thereby maintaining contact between the cam follower 107 and the crank wheel 105. When the cam follower 107 is in contact with or positioned on or against the surface of the portion of the crank lobe 106 that is past the peak of the crank lobe 106, the cam follower 107 causes the crank wheel 105 to continue to rotate without assistance from the drive piston 103 by applying a force to the crank lobe 106.

As described supra, the cam follower spring 108 applies force to the cam follower 107 to cause the cam follower 107 to maintain contact with the surface of the crank wheel 105. The crank wheel hub 109 is at the center of rotation for the crank wheel 105. The crank linkage 110 may connect the crank arm 111 to the crank wheel 105 and the piston linkage 112 may connect the crank arm 111 to the drive piston 103. As such, the crank arm 111 connects the drive piston 103 to the crank wheel 105 via the piston linkage 112 and the crank linkage 110.

FIGS. 6A-6E taken together illustrate operation of the vacuum or suction powered mechanism 100 utilizing an anti-stall crank mechanism 114.

FIG. 6A shows the drive piston 103 (shown in mid stroke) as it is being, driven from right to left by ambient air in the distal vacuum chamber 104 on the right side of the drive piston 103, and by suction on the left side of the drive piston 103 in the proximal vacuum chamber 102, thereby resulting in clockwise rotary motion of the crank wheel 105 via the crank arm ill connected to the drive piston 103. In the position shown in FIG. 6A, the drive piston 103 is not at a reversal point and is unlikely to stall. The cam follower 107 and cam lobes 106 are in neutral positions and are not interacting. The cam follower 107 is resting against the crank wheel 105 with no force or minimal force.

Figure 6B:
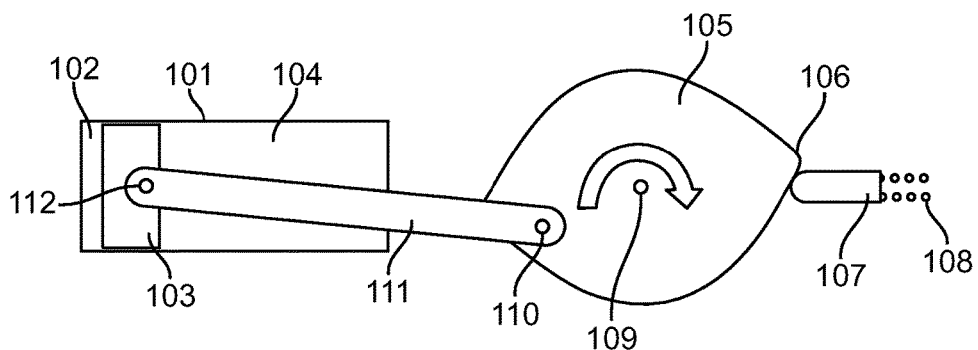

As shown in FIG. 6B, as the drive piston 103 approaches the top-dead-center stall position where the drive piston 103 reverses direction, the cam lobe 106 on the crank wheel 105 begins to push against the cam follower 107. This moves the cam follower 107 to the right, e.g., the cam follower 107 may be configured to slide or shift or be otherwise movable, e.g., in a manner as described below, thereby compressing the cam follower spring 108 and storing energy in the cam follower spring 108.

Figure 6C:
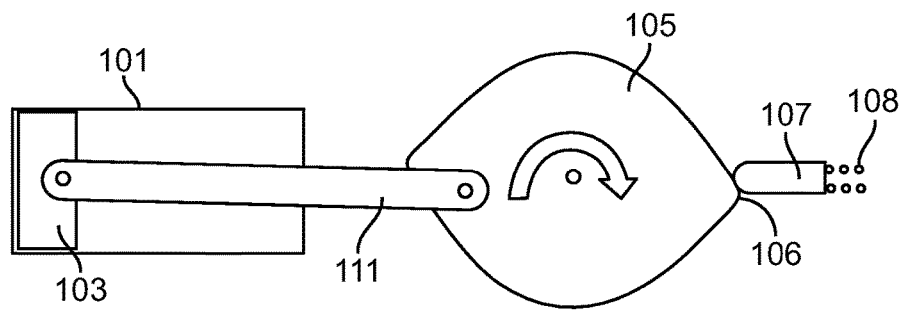

As shown in FIG. 6C, prior to the position where the drive piston 103 reverses direction (the top-dead-center position or the position where the vacuum powered mechanism may stall), the peak of the cam lobe 106 approaches the cam follower 107 and the cam follower 107 passes the peak of the cam lobe 106. The cam follower 107 is now exerting a force (by the energy stored in the cam follower spring 108) on the cam lobe 106 which drives the crank wheel 105 clockwise.

Figure 6D:
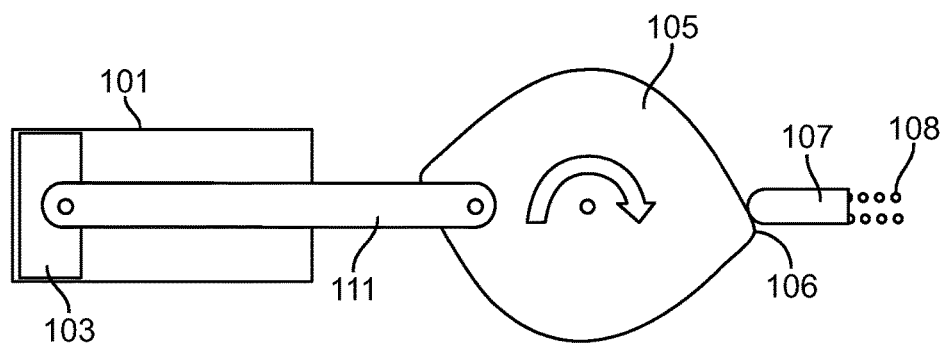

As shown in FIG. 6D, at the stall position (or top-dead-center position), e.g., where the piston linkage 112, crank arm 111, crank linkage 110, and crank wheel hub 109 are in alignment, the energy stored in the cam follower spring 108 continues to cause the cam follower 107 to exert a force on the cam lobe 106 which drives the crank wheel 105 clockwise. The rotation of the crank wheel 105 causes the drive piston 103 to move past the drive piston reversal point and into a position where it is unlikely to stall or does not stall.

Figure 6E:
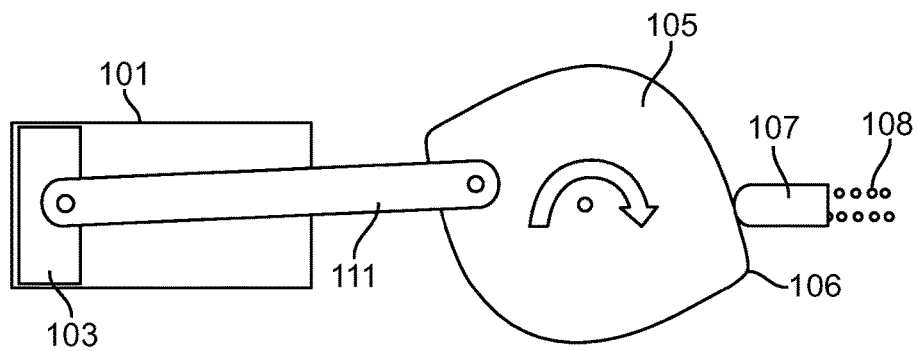
Figure 7A:
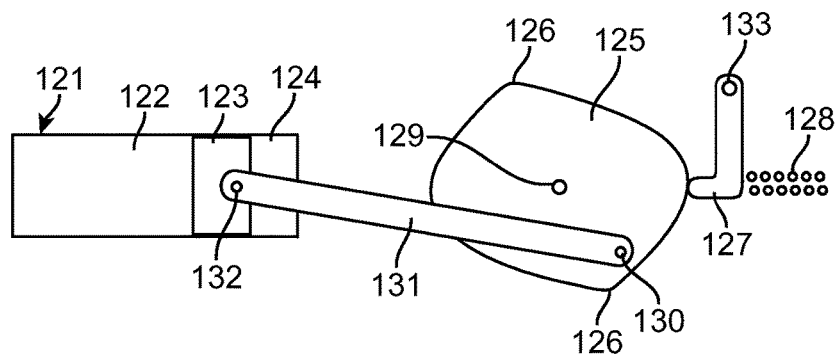
FIGS. 7A-7E illustrate a cross sectional side view of a variation of a vacuum or suction powered mechanism coupled to an anti-stall crank mechanism.
Figure 7B:
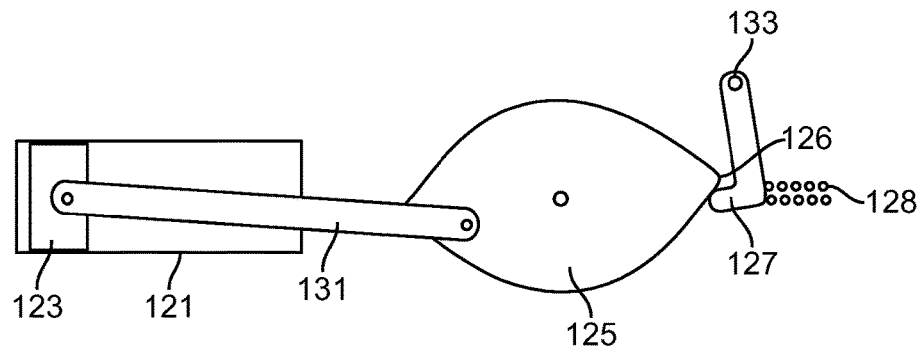
Figure 7C:
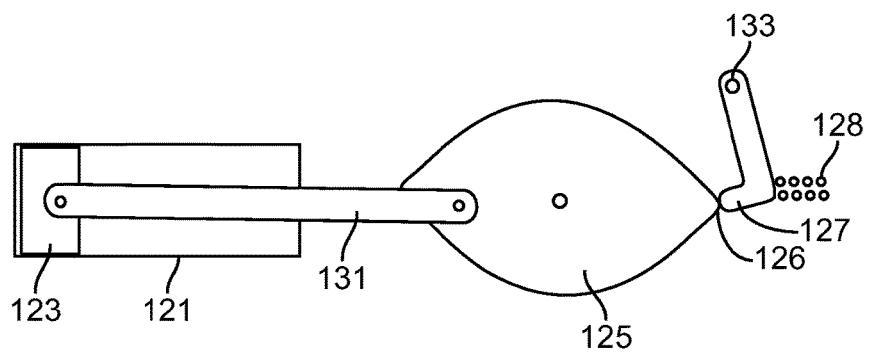
Figure 7D:
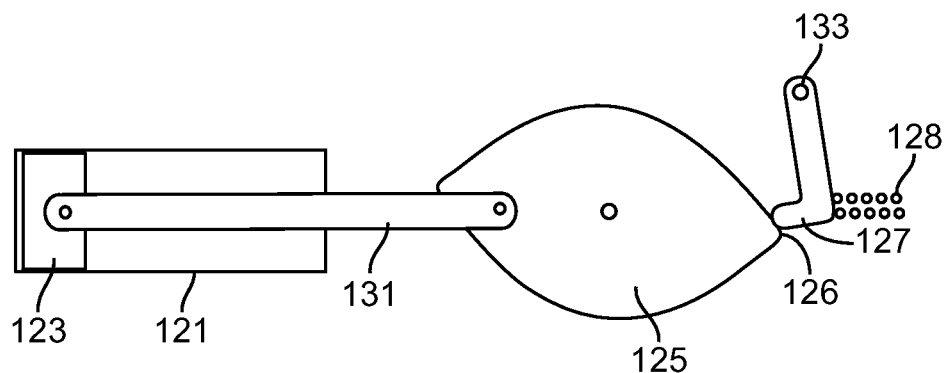
Figure 7E:
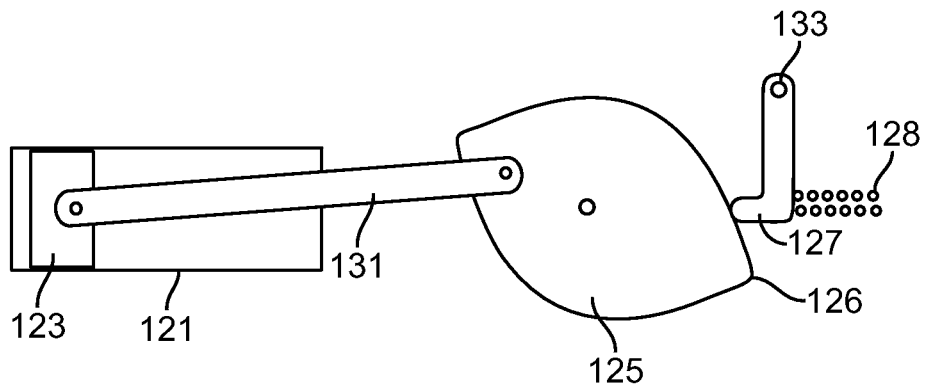
Figure 8A:
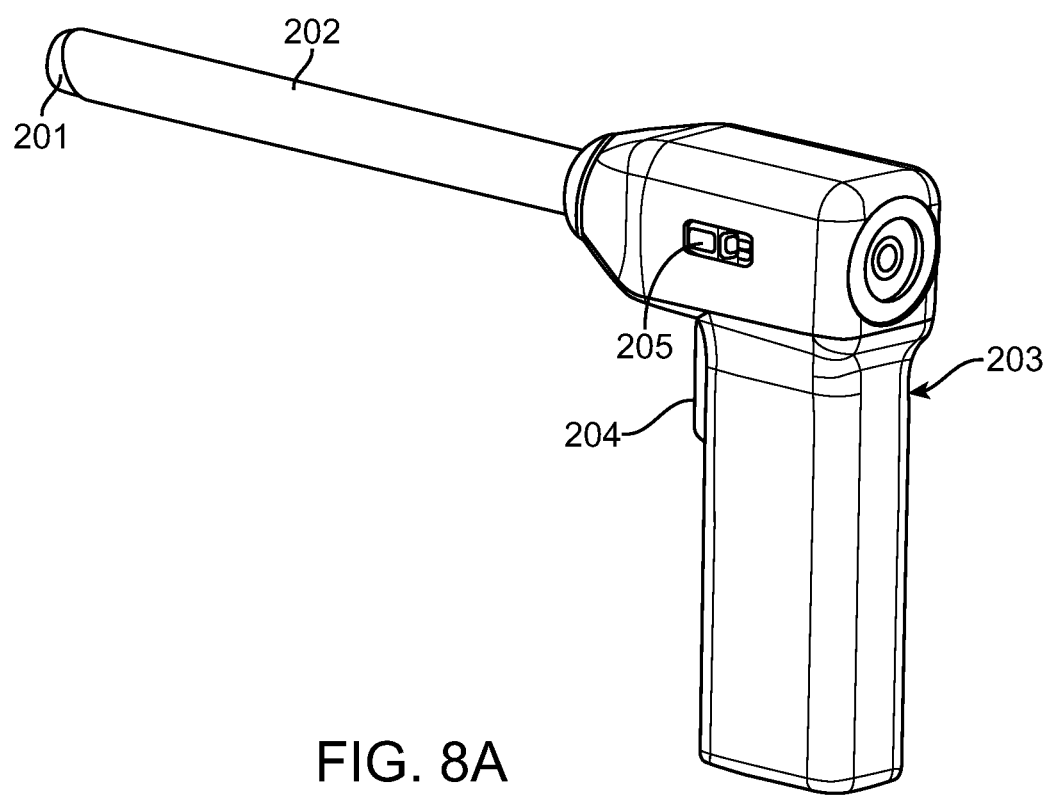
Figure 8C:
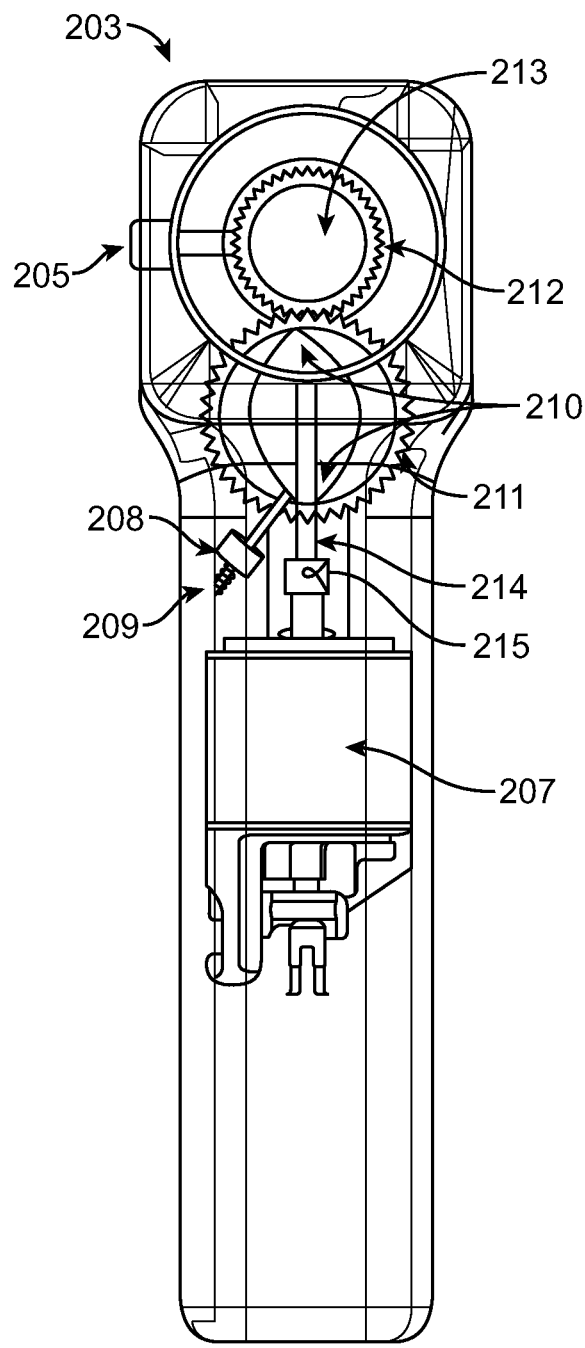
Figure 8D:
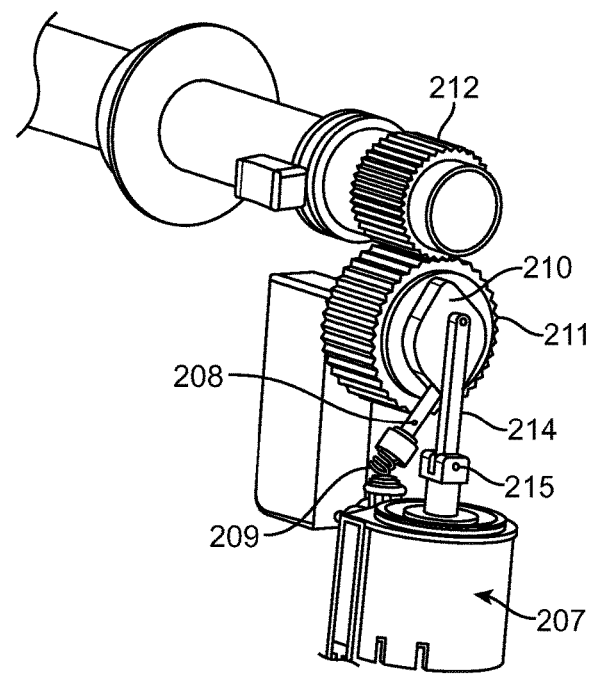
FIGS. 8D-8E illustrate a variation of a mechanism and/or component of the medical device of FIGS. 8A-8C.
Figure 8E:
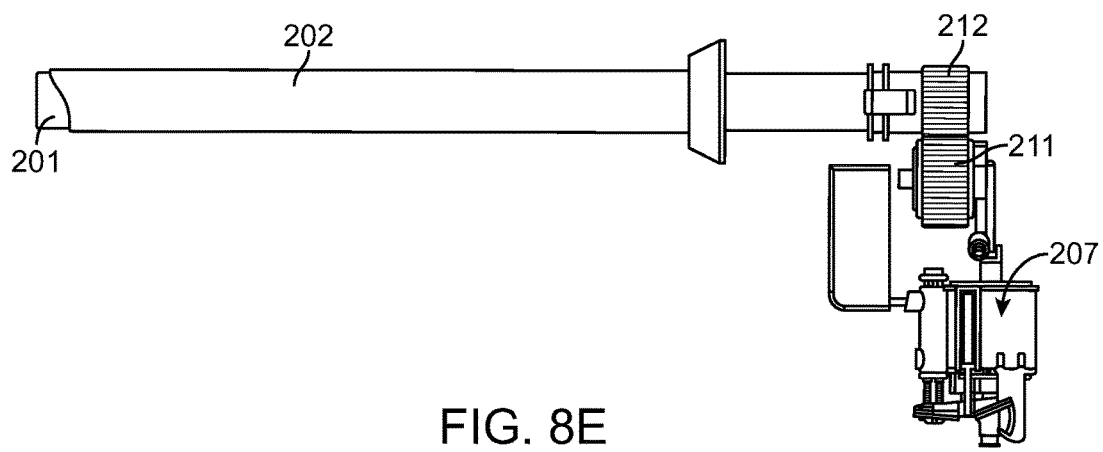

As shown in FIG. 6E, the crank mechanism 114 has moved past the stall position, and the cam follower 107 is no longer applying a force to the cam lobe 106 or to the crankshaft or crank arm 111. The drive piston 103 is able to advance left to right, thereby causing rotation of the crank wheel 105.

In certain variations, as shown in FIGS. 7A-7E, an anti-stall crank mechanism 120 may include a cam follower 127 that is hinged, allowing the cam follower 127 to rotate or pivot along the hinge 133 as it is shifted from left to right due to force applied to the cam follower 127 by the cam lobe 126. The cam follower 127 may also rotate along the hinge as it is moves from right to left as the cam follower 127 applies force supplied by the cam follower spring 128 to the crank wheel 125 and/or cam lobe 126. The crank wheel 125 may be rotated by the linear reciprocating motion of the drive piston 123 via the crank arm 121 and the force supplied by the cam follower 127 in a manner as described above. The rotation of the crank wheel 105 by the drive piston 123 and a force from the earn follower 127 and cam follower spring 128 causes the drive piston 103 to move past the drive piston reversal point and into a position where it is unlikely to stall or does not stall.

In certain variations, rather than the cam follower being, hinged, the cam follower arm may be elastic and the attachment point may be rigidly affixed rather than hinged. The elastic cam follower arm may serve to exert force on the crank wheel by forcing the cam follower surface against the crank wheel.

In certain variations, a method for preventing a vacuum powered mechanism from stalling is provided. A linear reciprocating drive piston of the vacuum powered mechanism is coupled to a cam or crank wheel and a cam follower. A cam follower may be used to exert a force on the crank wheel or cam surface, which causes the crank wheel or cam surface to translate into a position where the vacuum powered mechanism is unlikely to stall or does not stall when the drive piston of the mechanism reverses direction. An output of the vacuum powered mechanism may be rotary motion. The vacuum powered mechanism may be incorporated into a medical device, where translation of the cam or crank wheel produces a rotary motion for rotating an output shaft of the medical device to perform work on tissue.

Any of the various vacuum or suction powered mechanisms and/or various components or mechanisms for converting linear motion to rotary or rotating motion as described herein, e.g., such as the anti-stall crank mechanisms described above, may be incorporated into various medical devices to power those devices in order to perform work on tissue, e.g., such as any of the medical devices described herein or in the patent applications referenced herein. The vacuum or suction powered mechanism coupled to or including a mechanism or component for converting linear motion to rotary motion may be positioned in the handle, body or chamber of various medical devices, e.g., such as cutting devices described in the above referenced patent applications or the cutting devices having a rotating cutting shaft or tube described herein. Such devices could be fitted with a vacuum powered mechanism coupled to or including a component for converting the linear motion created by the vacuum powered mechanism into rotary motion (e.g., such as an anti-stall crank mechanism described herein). The devices may include a rotational output shaft coupled to the vacuum powered mechanism and/or component such as the anti-stall crank mechanism such that the rotary motion produced by the crank mechanism or other component is translated to the output shaft causing rotation of the output shaft or a tool or other operable element attached thereto to perform work on tissue. For example, the rotating output shaft may have a lumen and a sharpened distal end on or around at least a portion of the perimeter of the shaft to facilitate cutting and/or evacuation of tissue as described herein. Other devices may have a variety of designs and configurations suitable for incorporating the mechanisms and components described herein and coupling the mechanisms and components to an output shaft or operable element at a working end of the device to cause rotation or actuation of that output shaft or operable element to perform work on tissue, e.g., cutting and/or removal of tissue.

FIGS. 8A-8E illustrate an example of a medical device having a rotating cutting tube or shaft.

The device includes a shaft or inner tube 201. At least a portion of the distal extremity of the inner tube 201 may be sharpened to cut tissue that may be apposed, opposed or placed against the sharpened portion or blade of inner tube 201. The inner tube 201 may rotate along its longitudinal axis to cut tissue.

The device may also include a sheath or an outer tube 202. The outer tube may provide support to the inner tube (201) and act as a safety shield to prevent accidental tissue contact when the inner tube (1) is retracted within the lumen of the outer tube (202). The outer tube 202 may be stationary. The inner tube may be concentrically or coaxially positioned within the outer tube.

While the device illustrated in FIGS. 8A-8E illustrates a stationary outer tube 202 and a rotatable inner tube 201, it is contemplated that in other variations a device may include a stationary inner tube and a rotatable outer tube, where the outer tube may rotate along its longitudinal axis. In other variations, both the inner and outer tubes may be rotatable or only a single tube may be utilized.

The device may include a hand piece 203 or handle which serves as an operator interface portion of the device. The inner tube 201 and outer tube 202 may be coupled to the hand piece 203. The hand piece 203 may contain a motor or mechanism 207 or drive mechanism for rotating or driving the inner tube (201) and a control for advancing and/or retracting the inner tube (201) relative to the outer tube (202).

The device may include an inner tube position control 205. The inner tube position control provides a user interface to control the position of the inner tube 201 relative to the Outer Tube (202). For example, when the inner tube 201 is advanced distally, the distal end of the Inner Tube (201) may be fully exposed. When the inner tube 201 is in the intermediate position, the distal end of the Inner Tube (201) may be partially exposed relative to the end of the Outer Tube (202). When the inner tube 201 is advanced proximally, the inner tube (201) may be retracted within the Outer Tube (202) and may be positioned in a "safe" position where the cutting edge of the inner tube 1 is not exposed. The various positions of the inner tube may be achieved by actuating the inner tube position control 205 to cause movement of the inner tube 201.

While FIGS. 8A-8E illustrate a device where the inner tube is translatable axially or translatable along its longitudinal axis and the outer tube is stationary axially or not translatable along its longitudinal axis, it is contemplated that in other variations, the inner tube may be stationary axially or not translatable along its longitudinal axis and the outer tube may be translatable axially or translatable along its longitudinal axis. The position of the outer tube relative to the inner tube may be controlled, e.g., the outer tube may be advanced or retracted to fully expose, partially expose or cover the cutting edge, distal end or distal portion of the inner tube. The various positions of the outer tube may be achieved by actuating an outer tube position control to cause movement of the outer tube. In the variations described above, a device may include one or more inner or outer tube positional options, e.g., three options. Optionally, the tube position control may include an indicator which indicates the length of tube advancement.

A proximal seal 206 may be located at the proximal end of the inner tube 201. The proximal seal 206 may allow the passage of various medical devices, instruments or tools through the lumen 213 of the inner tube (201) to gain access to the operative space distal to the device without allowing insufflation gas or other fluid to escape through the lumen 13 of the inner tube (201). Inner lube (201) includes a lumen 213 wherein medical instruments may be passed from the proximal end of the device and to or out of the distal end of the device, to the distal space or location within the body cavity and/or the space or location where tissue may be drawn from the distal space or location to remove it from the body.

The device may also include one or more triggers 204 for providing ON/OFF control for the motor or mechanism (207). The mechanism 207 may use suction or vacuum as a power source to produce linear reciprocating motion, as described herein. The suction or vacuum may be provided by an external source of suction or vacuum coupled to the mechanism. The linear reciprocating motion may be converted into rotational motion to rotate the inner Tube (201).

As shown in FIGS. 8A-8E, the mechanism 207 may include or be coupled to a cam or cam having cam lobes 210. The cam or cam lobes 210 may be coupled to a gear or meshing gear 211 and the cam or cam lobes 210 may rotate with the meshing gear (211). As the cam or cam lobes 210 rotate they may interact with or come into contact with a cam follower (206) which ensures that the mechanism 207, cam lobes, and/or gears continue to move or rotate past the "top-dead-center" and "bottom-dead-center" potential stall positions.

A cam follower 208 may provide a linear force on a cam surface or cam lobes (210) to prevent the mechanism 207, cam lobes, and/or gears from stalling in the "top-dead-center" and "bottom-dead-center" positions. A cam follower spring 209 may provide a linear force on a cam follower (208) which may provide a linear force on a cam or cam lobe 210. The cam follower spring 209 may allow the cam follower (208) to move linearly to maintain contact with the cam or cam lobes (210).

The meshing gear 211 may be coupled to the mechanism 207 via a crank shaft or crank arm 214. The meshing gear 211 may also be coupled to or in contact with another gear or driven gear (212). The meshing gear 211 is driven by the crank arm 214 to translate linear motion to rotary motion, and the rotary motion of the meshing gear 211 drives the driven gear 212 in a rotary motion. Rotation of the Driven Gear 212 causes rotational motion of the Inner Tube (201) coupled to the driven gear 212, in other variations, the driven gear 212 may be driven by the meshing gear (211) to cause rotational motion of an outer tube (201) coupled to the driven gear 212.

As stated supra, the meshing gear 211 may be driven by the crank shaft or Crank Arm (214) to translate linear motion produced by the mechanism 207 into rotary motion of the meshing gear 211. The crank arm 214 may be connected to the suction or vacuum powered mechanism (207) by a Crank Arm Linkage (215). The crank arm 214 converts linear motion produced by the suction or vacuum powered mechanism (207) to rotary motion by causing the Meshing Gear (211) to rotate. The crank arm linkage 215 may connect the Crank Arm (214) to the suction or vacuum powered mechanism (207) and allow the Crank Arm (214) to pivot relative to the Suction or vacuum powered mechanism (207).

In certain variations, a medical device is provided which is connected to a source of vacuum or suction which provides power for a motor or mechanism of the device that has a linear output. The linear output of the motor may be converted to rotating output on an output shaft by a crank mechanism connected to the output of the vacuum motor. The crank may be connected to the output shaft of the device, thereby causing rotary motion on the output shaft of the medical device. The output shaft may perform the intended function of the medical device such as cutting or drilling tissue. The crank mechanism may have lobes that interact with a cam follower wherein the cam follower applies a force on the lobe to move the crank or crank wheel past a stalled position.

In certain variations, a medical device that is connected to a source of vacuum or suction which provides power for a motor or mechanism of the device may have a linear output. The linear output of the motor may be converted to rotating output on an output shaft by a crank mechanism connected to the output shaft of the vacuum motor. The crank mechanism is connected to the output shaft of the device, thereby causing rotary motion of the output shaft of the medical device. The output shaft may perform the intended function of the medical device such as cutting or drilling tissue. The crank mechanism may include lobes on a crank wheel that interact with a spring loaded pawl wherein the pawl mechanism applies a force on a lobe to move the crank and/or crank wheel past a stalled position.

In the variations described herein, a method for preventing a vacuum powered motor or mechanism from stalling when the drive piston of the mechanism reverses direction may include using a cam follower to exert a force on a cam or crank wheel surface thereby causing the cam or crank wheel, which is coupled to the drive piston, to translate into a position where the vacuum powered mechanism is unlikely to stall or will not stall.

In certain variations, a medical device or cutting device may be powered by a vacuum powered mechanism comprised of a cam follower that exerts a force on a cam surface thereby causing the cam surface to translate into a position where the vacuum powered mechanism is unlikely to stall.

In any of the variations described herein, the vacuum powered mechanism may be powered solely by suction or solely by suction created by a vacuum source without the need for any other source of power.

Mechanisms or motors powered by suction from a vacuum source are useful for powering medical devices because sources of suction or vacuum are readily available in operating rooms and clinics where surgical procedures are performed. Certain applications may require linear actuation of a tissue effector or operable element, e.g., a cutting blade moving past an anvil to slice tissue. Other applications may require rotary motion, e.g., to rotate drills, cutters and/or burrs. Therefore, in certain variations it is necessary to convert the linear motion or linear output produced from suction or vacuum powered mechanisms or motors into rotary motion.

Figure 9:
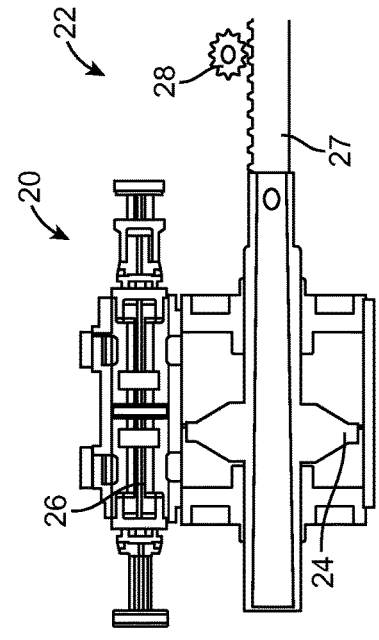
FIGS. 9-11 show cross sections of a variation of a vacuum or suction powered mechanism coupled to a component for converting linear reciprocating motion to rotational motion, including a rack and pinion gear.
Figure 10:
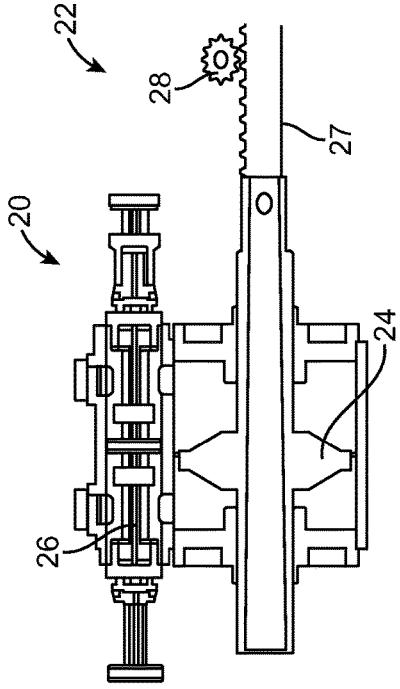
Figure 11:
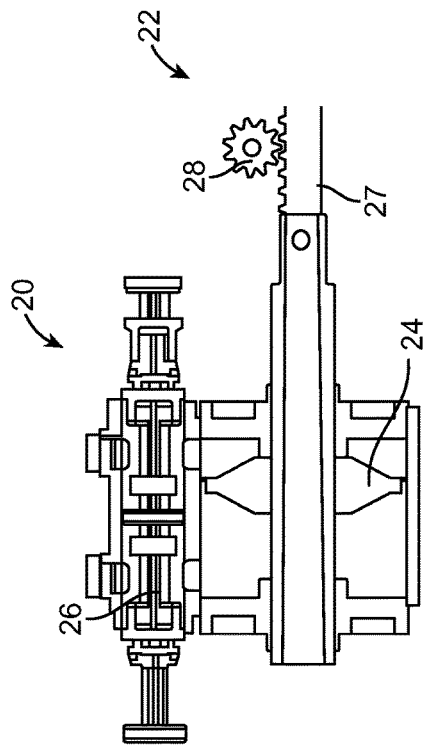

FIGS. 9-11 show another variation of a mechanism powered by suction from a vacuum or suction source, where the mechanism is coupled to or includes a component for converting linear reciprocating motion to rotating or rotary motion. The mechanism 20 may include a drive piston 24 and a shuttle piston 26. The drive piston 24 may be coupled or connected to a rack and pinion drive 22. Optionally, the drive piston 24 may be coupled to an output shaft which is connected to or coupled to a rack and pinion drive 22.

Suction created by the vacuum or suction source causes the drive piston 24 to reciprocate linearly back and forth. The back and forth linear reciprocation of the drive piston 24 of the mechanism 20 causes the rack 27 to reciprocate linearly back and forth. Optionally, the drive piston 24 may cause an output shaft to reciprocate linearly back and forth, which causes the rack 27 to reciprocate linearly hack and forth. The rack 27 engages the pinion gear 28 and the linear reciprocating motion of the rack 27 drives the pinion gear 28 to rotate in alternating directions depending on the direction of motion of the rack 27. For example, when the rack 27 moves from a proximal position to a distal position (left to right when viewing the figures), the pinion gear 28 rotates counter-clockwise. When the rack 27 moves from a distal position to a proximal position (right to left when viewing the figures), the pinion gear 28 rotates clockwise. The linear reciprocating back and forth motion produced by the mechanism 20 causes the pinion gear 28 to rotate in alternating clockwise and counterclockwise directions, thereby generating or producing an oscillating rotating motion or convening the linear reciprocation motion into oscillating rotating motion. The produced oscillating rotary or rotational motion may cause an output shaft or tool of a device to rotate, e.g., an output shaft which performs work on a tissue or causes a tool to perform work on tissue.

FIG. 9 shows the suction powered mechanism 20 driving a rack and pinion gear drive 22, where the rack 27 is in a proximal driving position.

FIG. 10 shows the suction powered mechanism 20 driving a rack and pinion gear drive 22, where the rack 27 is in a midpoint driving position.

FIG. 11 shows the suction powered mechanism 20 driving a rack and pinion gear drive 22, where the rack 27 is in a distal driving position.

FIG. 12A-12D illustrate another example of a medical device having a rotating cutting tube or shaft.

The device includes a shaft or inner tube 301. At least a portion of the distal extremity of the inner tube 301 may be sharpened to cut tissue that may be apposed, opposed or positioned against the sharpened portion or blade of inner tube 301. The inner tube 301 may rotate along its longitudinal axis to cut tissue.

The device may also include a sheath or outer tube 302. The outer tube may provide support to the inner tube (301) and act as a safety shield to prevent accidental tissue contact when the inner tube (301) is positioned within the lumen of the outer tube (302). The inner tube 1 may be concentrically or coaxially positioned within the outer tube 302.

While the device illustrated in FIGS. 12A-12D illustrates a stationary outer tube 302 and a rotatable inner tube 301, it is contemplated that in other variations a device may include a stationary inner tube and a rotatable outer tube, where the outer tube may rotate along its longitudinal axis. In other variations, both the inner and outer tubes may be rotatable or only a single tube may be utilized.

The device may include a hand piece 303 or handle which serves as an operator interface portion of the device. The inner tube 301 and outer tube 302 may be coupled to the hand piece 303. The hand piece 303 may contain a motor or mechanism 307 or drive mechanism for rotating or driving the inner tube (301) and a control for advancing and/or retracting the outer tube (302) relative to the inner tube (301).

The device may include an outer tube position control 318. The outer tube position control 318 provides a user interface to control the position of the outer tube 302 relative to the inner Tube (331). For example, when outer tube position control 318 is rotated in a first direction, outer tube 302 may be retracted proximally such that the distal end of the Inner Tube (301) is fully exposed. When outer tube position control 318 is rotated to a second middle or intermediate position, the distal end of the Inner Tube (301) may be partially exposed relative to the end of the Outer Tube (302). When the outer tube position control 318 is rotated to a third position, the outer tube 302 may be advanced distally and may be positioned in a "safe" position where the cutting edge of the inner tube 301 is not exposed and is fully covered or shielded.

A Saddle or attachment 319 may be fixedly attached to the outer Tube (302) to translate rotary motion from the outer Tube Position Control (318) to linear motion of the outer Tube (302) to change the position of the outer Tube (302) relative to the inner Tube (301).

Figure 12A:
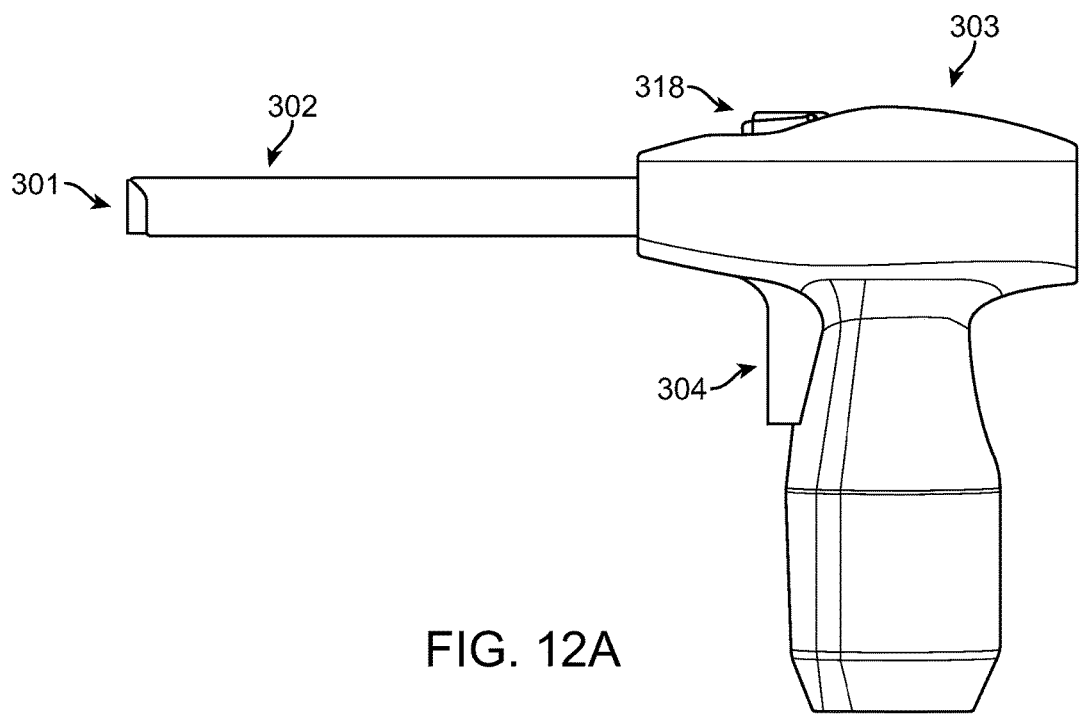
FIGS. 12A-12C illustrate a variation of a medical device having a oscillating rotating cutting tube or shaft where the device is powered by a vacuum powered mechanism.
Figure 12B:
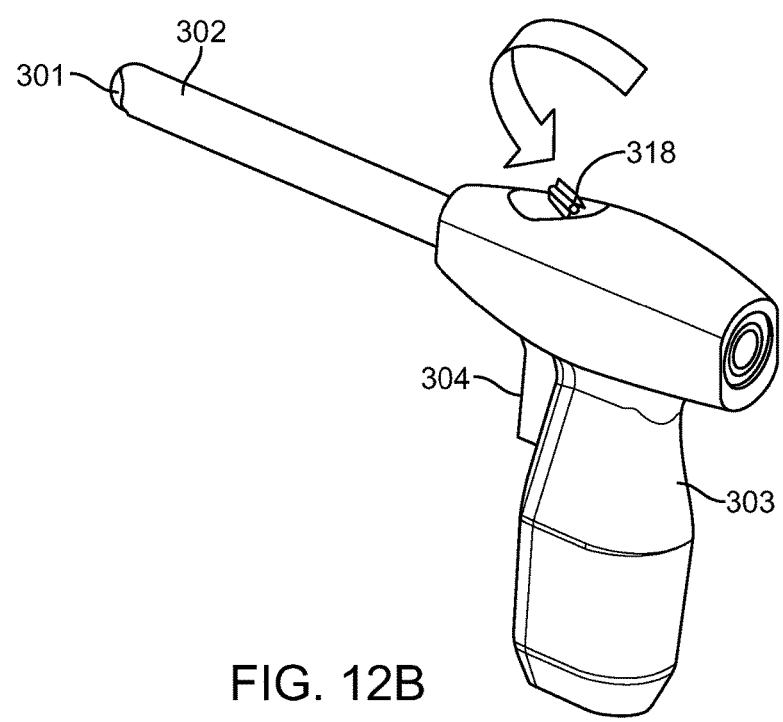
Figure 12C:
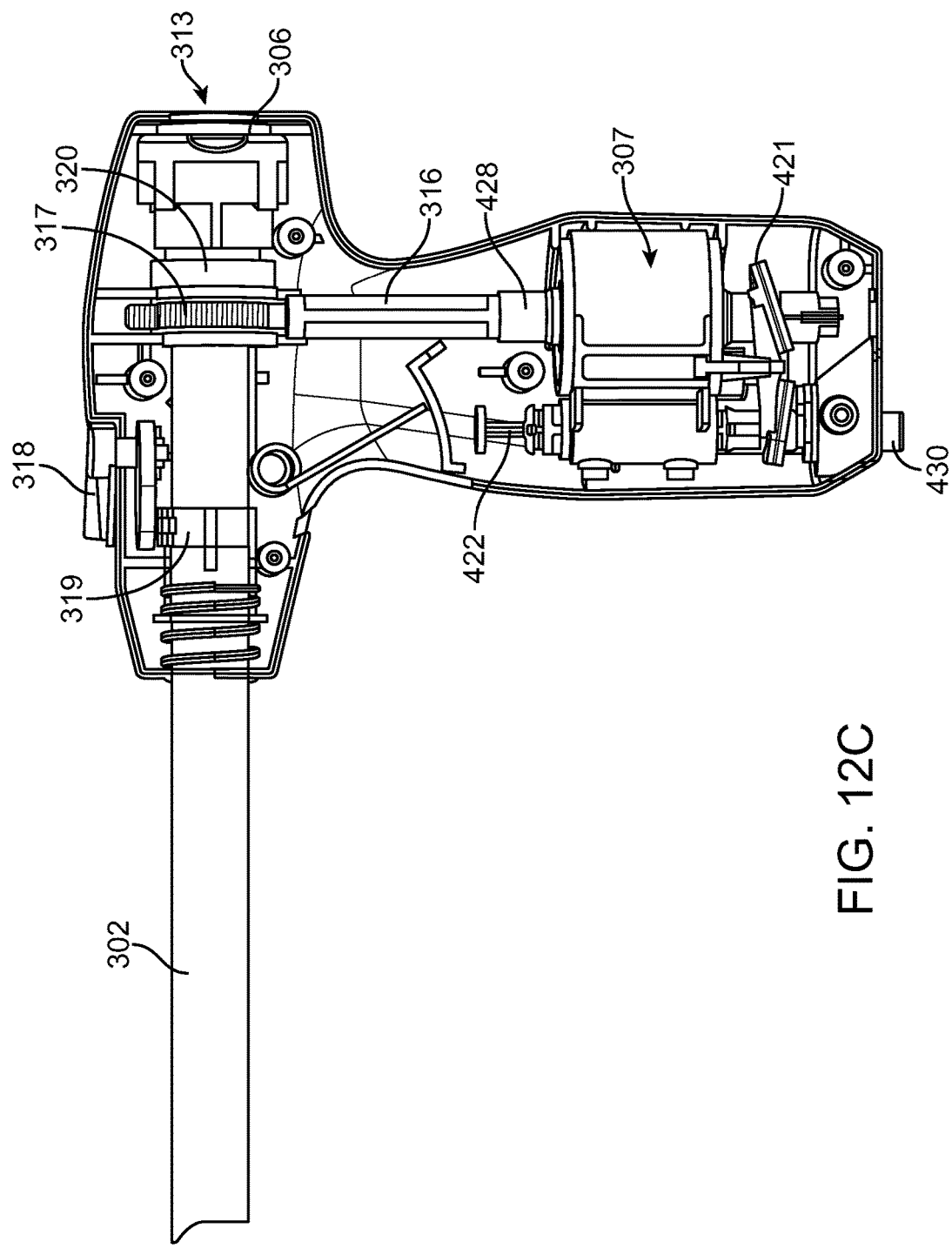
Figure 12D:
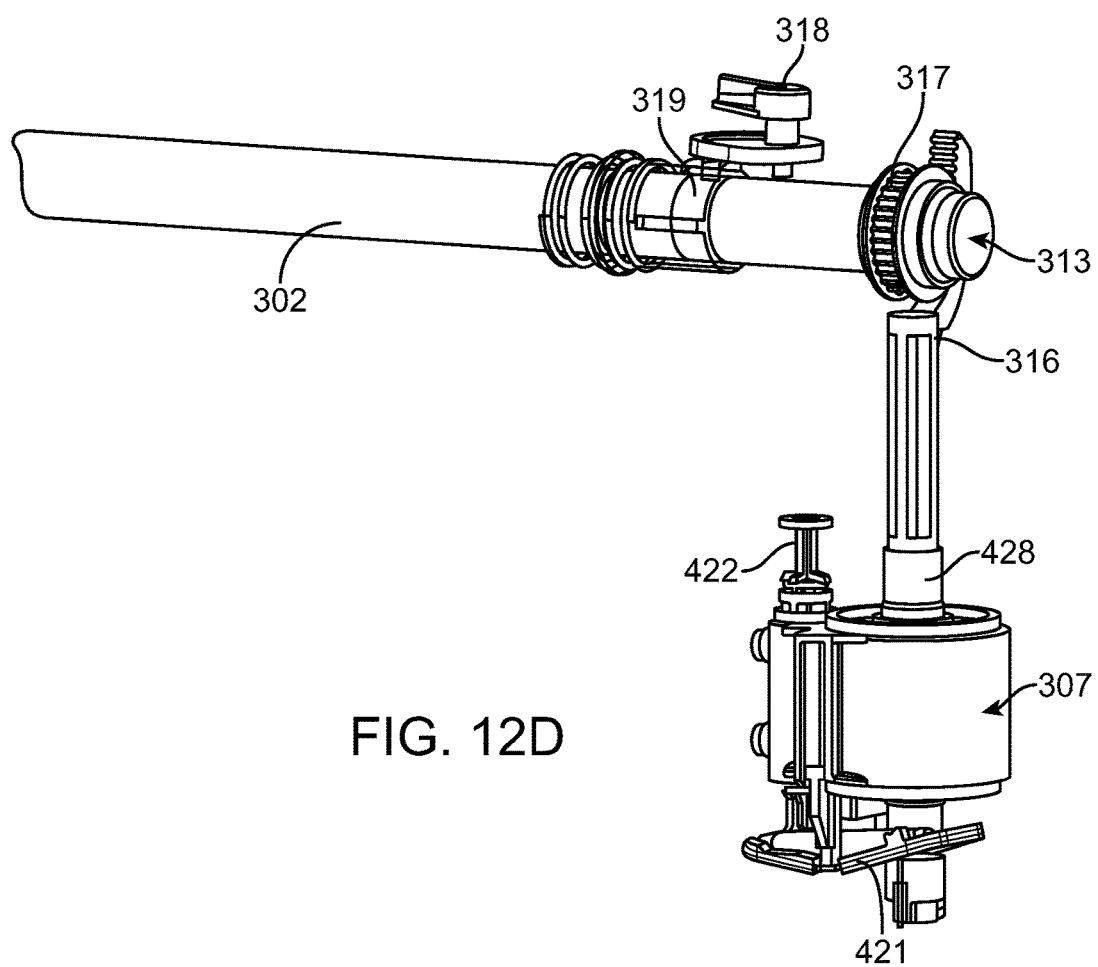
FIG. 12D illustrates a variation of a mechanism and/or component of the medical device of FIGS. 12A-12C.
Figure 13:
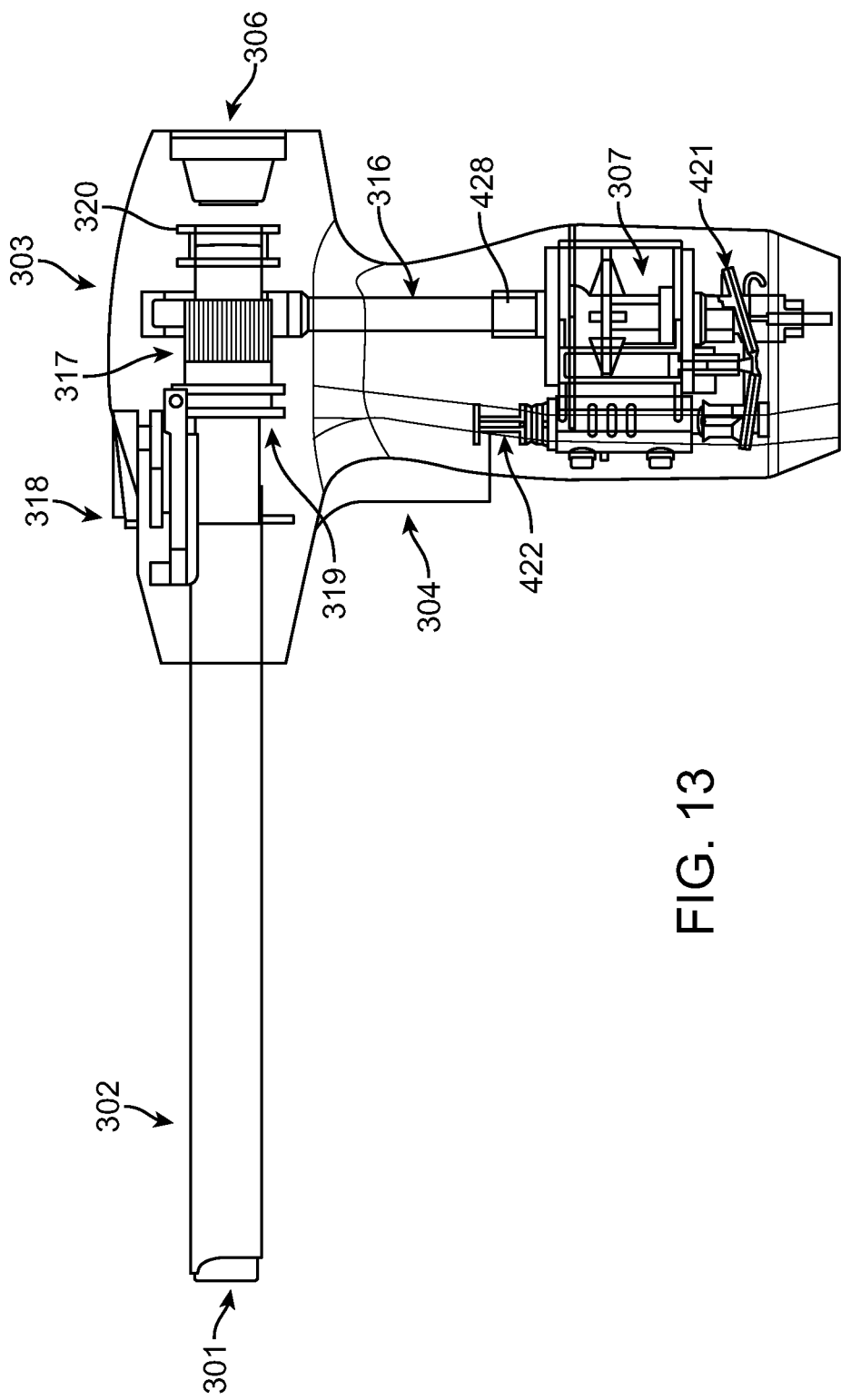
FIG. 13 illustrates a variation of a medical device having an oscillating rotating cutting rube or shaft where the device is powered by a vacuum powered mechanism.
Figure 14A:
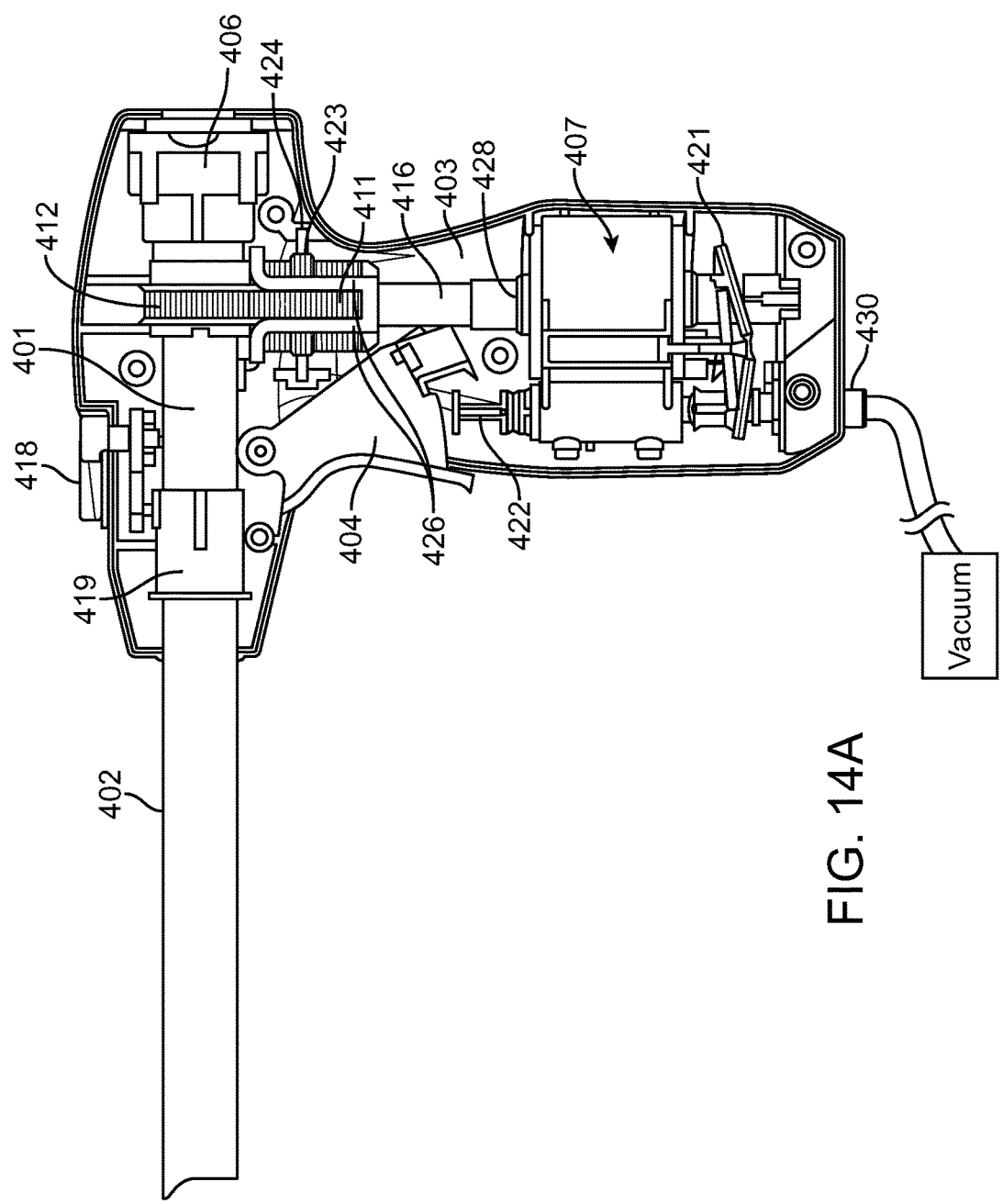
FIGS. 14A-14C illustrate a variation of a medical device having an oscillating rotating cutting tube or shaft where the device is powered by a vacuum powered mechanism.
Figure 14B:
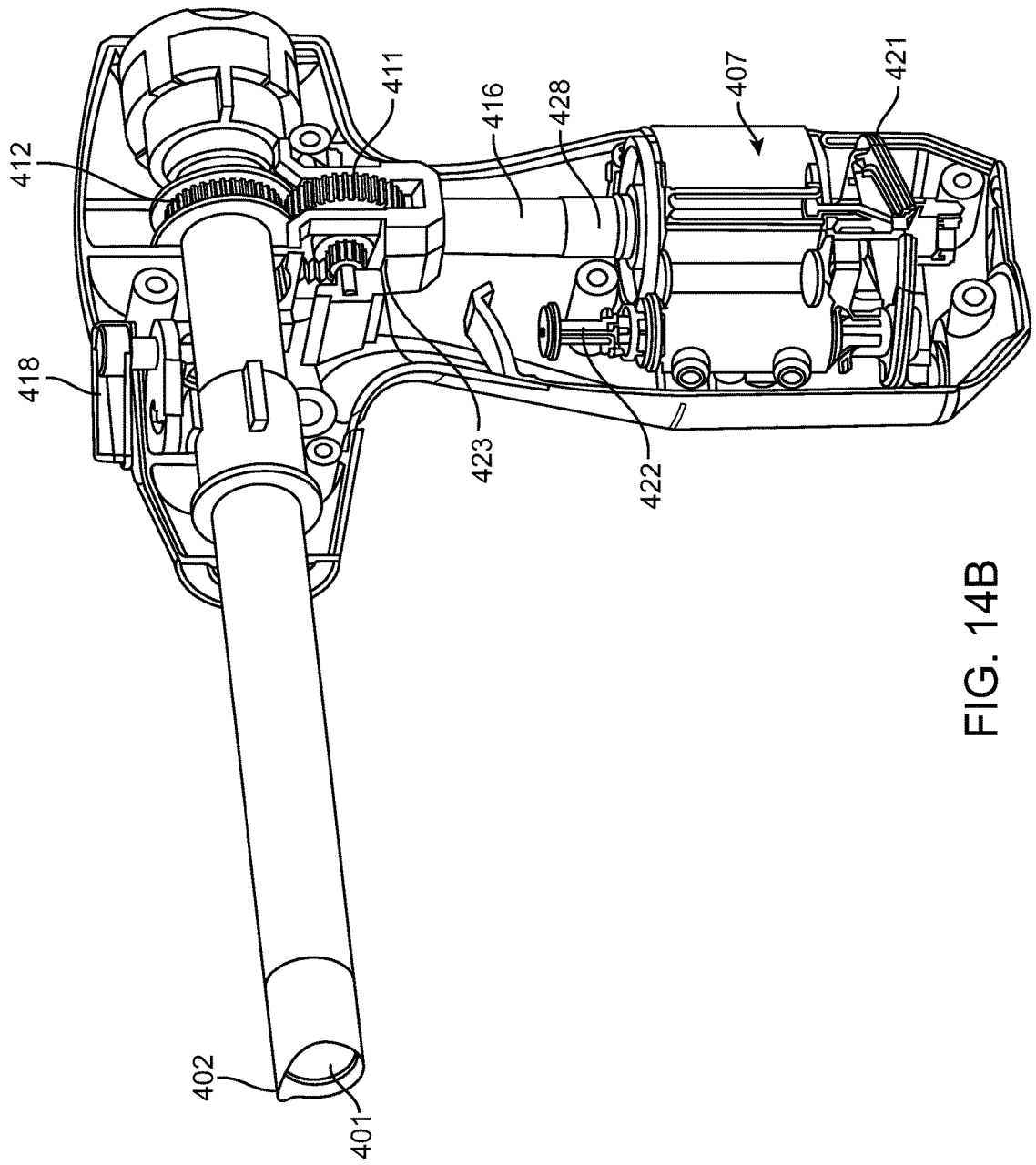
Figure 14C:
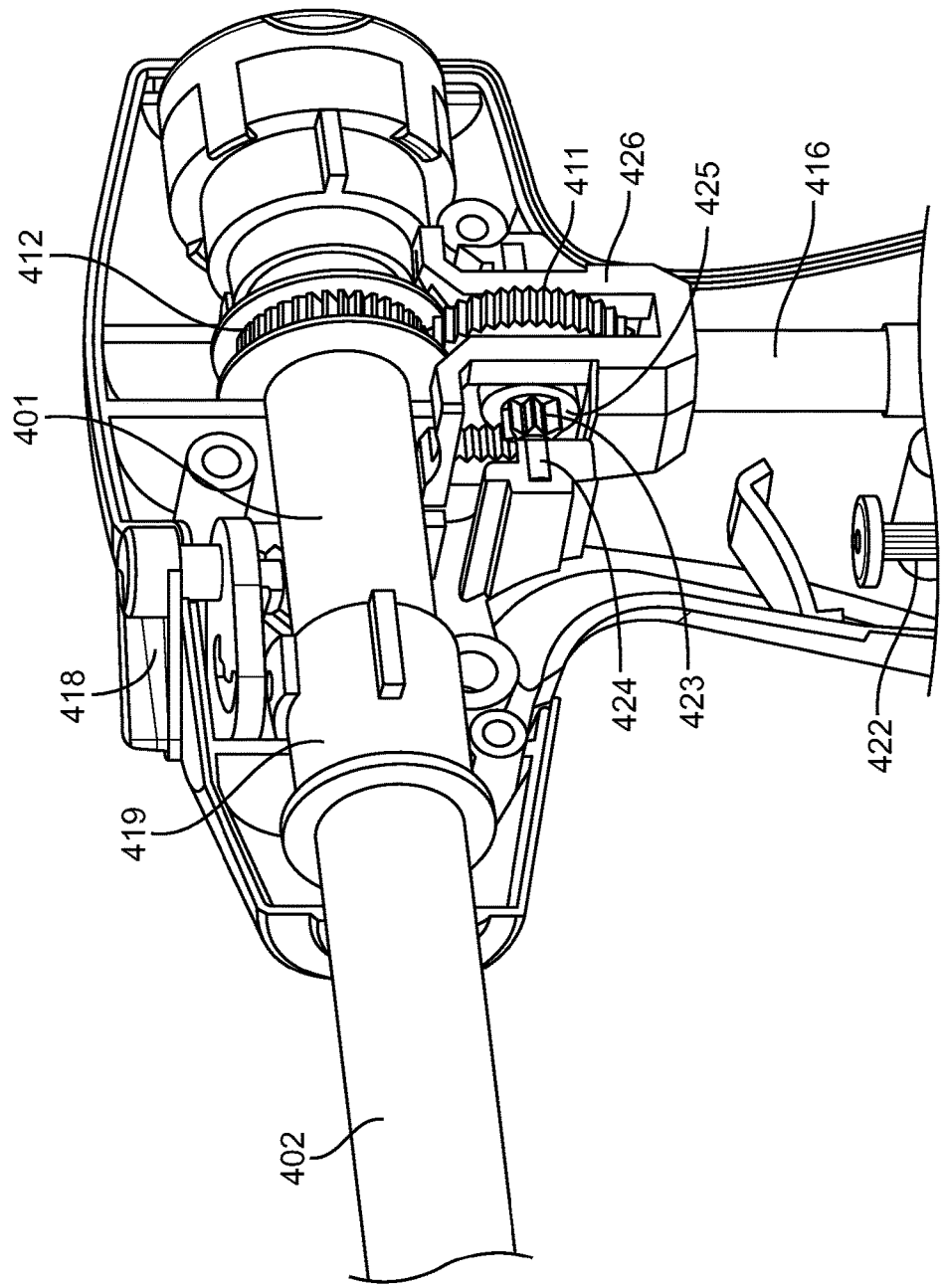
Figure 14D:
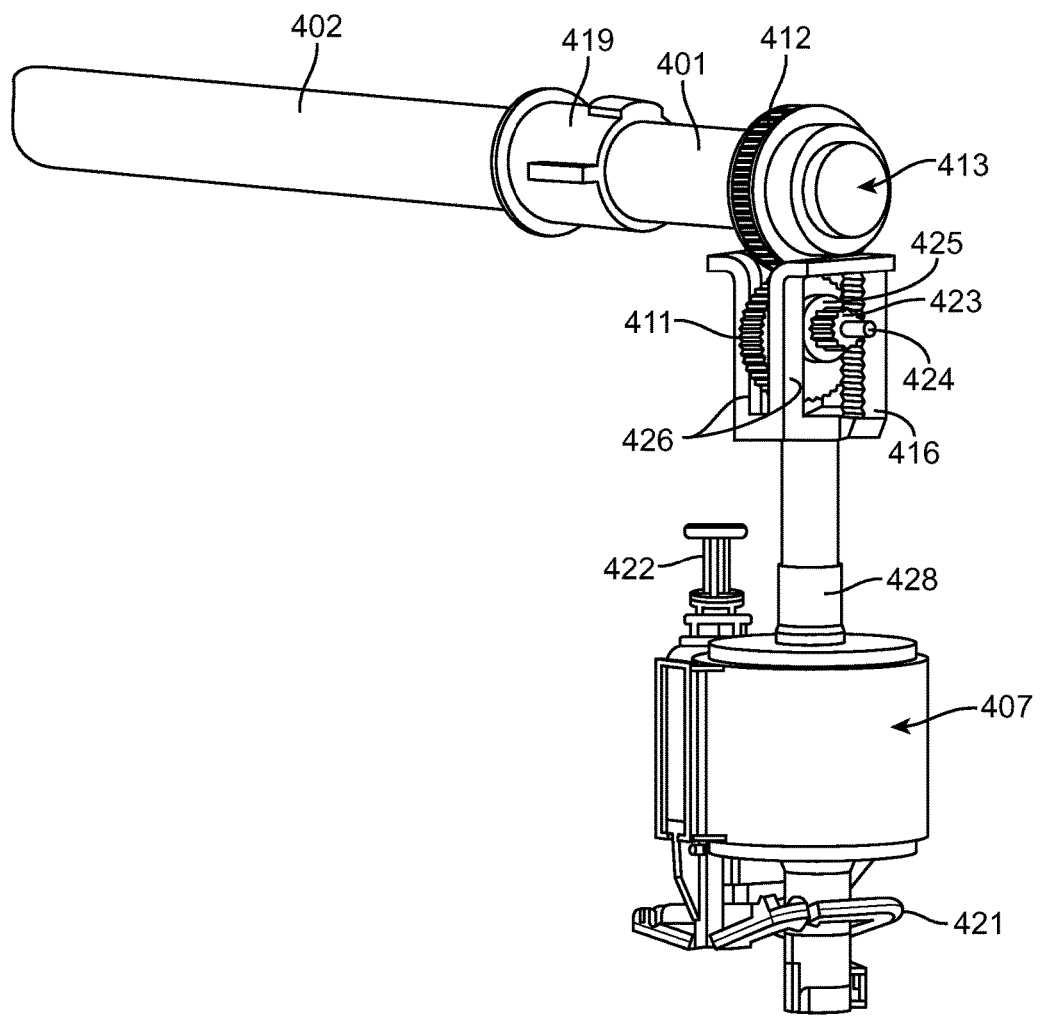
FIGS. 14D-14F illustrate a variation of a mechanism and/or component of the medical device of FIGS. 14A-14C.
Figure 14E:
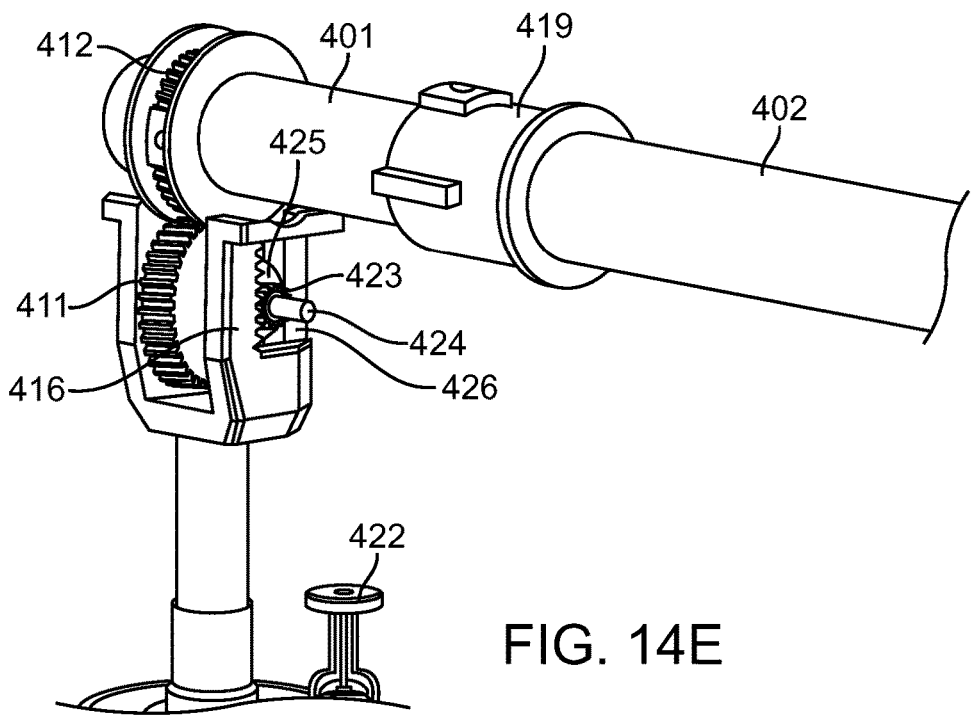
Figure 14F:
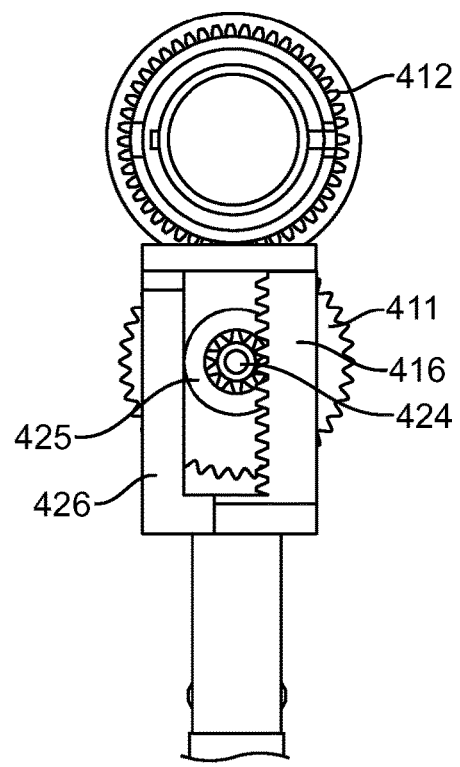

While FIGS. 12A-12D illustrate a device where the outer tube is translatable axially or translatable along its longitudinal axis and the inner tube is stationary axially or not translatable along its longitudinal axis, it is contemplated that in other variations, the outer tube may be stationary axially or not translatable along its longitudinal axis and the inner tube may be translatable axially or translatable along its longitudinal axis (See e.g., FIG. 13). The position of the inner tube 301 relative to the outer tube 302 may be controlled, e.g., the inner tube 1 may be advanced, or retracted to fully expose, partially expose or shield the cutting edge, distal end or distal portion of the inner tube 301. The various positions of the inner tube 1 may be achieved by actuating an inner tube position control to cause movement of the inner tube. In the variations described above, a device may include one or more inner or outer tube positional options, e.g., three options. Optionally, the tube position control may include an indicator which indicates the length of tube advancement.

The medical device may also include a proximal seal 306. The proximal seal 306 may allow the passage of various medical devices, instruments or tools through the lumen 313 of the inner tube (301) to gain access to the operative space distal to the device without allowing insufflation gas or other fluid to escape through the device or the lumen 313 of the inner tube (301). Inner Tube (301) includes a lumen 313 wherein medical instruments may be passed from the proximal end of the device and to or out of the distal end of the device, to the distal space or location within the body cavity and/or the space or location where tissue may be drawn from the distal space or location to remove it from the body.

A Bushing or sleeve 320 may support the proximal end of the Inner Tube (301) to maintain rotational stability. The bushing or sleeve 320 may also provide a seal to prevent gas or other fluid leakage through the Inner Tube (301).

The device may also include one or more triggers 4 for providing ON/OFF control for the motor or mechanism (307). The mechanism 307 may use suction or vacuum as a power source to produce linear reciprocating motion, as described herein. The suction or vacuum may be provided by an external source of suction or vacuum coupled to the mechanism. The linear reciprocating motion may be converted into rotational motion to rotate the Inner Tube (301).

As shown in FIG. 12C-12D, the mechanism 307 may include or be coupled to one or more racks 316. The rack 316 may be coupled, e.g., attached directly, to the suction or vacuum powered mechanism (307). The vacuum or suction powered mechanism 307 produces a linear reciprocating motion which causes the rack (316) to reciprocate linearly and to drive one or more Pinion Gears (317) in an oscillating rotary motion or to cause the pinion gear 317 to reversibly rotate back and forth. The pinion gear 317 may be driven by the Rack (316) to rotationally oscillate or reversibly rotate the Inner Tube (301) which is coupled to the pinion gear 317. As a result, the rack and pinion gear causes oscillating rotation of the inner tube, such that the inner tube rotates back and forth to produce a "sawing" type oscillating rotary cutting motion at its distal end.

FIG. 14A-14F illustrate another example of a medical device having a rotating cutting tube or shaft.

The device includes a shaft or inner tube 401. At least a portion of the distal extremity of the inner tube 401 may be sharpened to cut tissue that may be apposed, opposed or positioned against the sharpened portion or blade of inner tube 401. The inner tube 401 may rotate along its longitudinal axis to cut tissue.

The device may also include a sheath or outer tube 402. The outer tube may provide support to the inner tube (401) and act as a safety shield to prevent accidental tissue contact when the inner tube (401) is positioned within the lumen of the outer tube (402). The inner tube 401 may be concentrically or coaxially positioned within the outer tube 402.

While the device illustrated in FIGS. 14A-14E illustrates a stationary outer tube 402 and a rotatable inner tube 401, it is contemplated that in other variations a device may include a stationary inner tube and a rotatable outer tube, where the outer tube may rotate along its longitudinal axis. In other variations, both the inner and outer tubes may be rotatable or only a single tube may be utilized.

The device may include a hand piece 403 or handle which serves as an operator interlace portion of the device. The inner tube 401 and outer tube 402 may be coupled to the hand piece 403. The hand piece 403 may contain a motor or mechanism 407 or drive mechanism for rotating or driving the inner tube (401) and a control for advancing and/or retracting the outer tube (402) relative to the inner tube (401).

The device may include an outer tube position control 418. The outer tube position control 418 provides a user interface to control the position of the outer tube 402 relative to the inner Tube (401). For example, when outer tube position control 418 is rotated in a first direction, outer tube 402 may be retracted proximally such that the distal end of the Inner Tube (401) is fully exposed. When outer tube position control 418 is rotated to a second middle or intermediate position, the distal end of the Inner Tube (401) may be partially exposed relative to the end of the Outer Tube (402). When the outer tube position control 418 is rotated to a third position, the outer tube 402 may be advanced distally and may be positioned in a "safe" position where the cutting edge of the inner tube 401 is not exposed and is fully covered or shielded.

A Saddle or attachment 419 may be fixedly attached to the outer Tube (402) to translate rotary motion from the outer Tube Position Control (418) to linear motion of the outer Tube (402) to change the position of the Outer Tube (402) relative to the inner Tube (401).

While FIGS. 14A-14F illustrate a device where the outer tube is translatable axially or translatable along its longitudinal axis and the inner tube is stationary axially or not translatable along its longitudinal axis, it is contemplated that in other variations, the outer tube may be stationary axially or not translatable along its longitudinal axis and the inner tube may be translatable axially or translatable along its longitudinal axis. The position of the inner tube 401 relative to the outer tube 402 may be controlled, e.g., the inner tube 401 may be advanced or retracted to fully expose, partially expose or shield the cutting edge, distal end or distal portion of the inner tube 401. The various positions of the inner tube 401 may be achieved by actuating, an inner tube position control to cause movement of the inner tube. In the variations described above, a device may include one or more inner or outer tube positional options, e.g., three options. Optionally, the tube position control may include an indicator which indicates the length of tube advancement.

The medical device may also include a proximal seal 406. The proximal seal 406 may allow the passage of various medical devices, instruments or tools through the lumen 413 of the inner tube (401) to gain access to the operative space distal to the device without allowing insufflation gas or other fluid to escape through the device or the lumen 413 of the inner tube (401). Inner Tube (401) includes a lumen 413 wherein medical instruments may be passed from the proximal end of the device and to or out of the distal end of the device, to the distal space or location within the body cavity and/or the space or location where tissue may be drawn from the distal space or location to remove it from the body.

A Bushing or sleeve 420 may support the proximal end of the Inner Tube (401) to maintain rotational stability. The bushing or sleeve 420 may also provide a seal to prevent gas or other fluid leakage through the Inner Tube (401).

The device may also include one or more triggers 404 for providing ON/OFF control for the motor or mechanism (407). The mechanism 407 may use suction or vacuum as a power source to produce linear reciprocating motion, as described herein. The suction or vacuum may be provided by an external source of suction or vacuum coupled to the mechanism. The linear reciprocating motion may be converted into rotational motion to rotate the Inner Tube (401).

The mechanism 407 may be coupled to a rack and gear assembly having one or more racks and one or more gears. The vacuum or suction powered mechanism 407 produces a linear reciprocating motion which causes a rack 416 to reciprocate linearly and to drive a Pinion Gear (423) in an oscillating rotary motion or to cause the pinion gear 423 to reversibly rotate back and forth. The Rack (416) may have one or more Rack Columns (426) contacting one or more Free Wheel (425) and extending on the side opposite the Pinion Gear (423). The contact between the Rack Columns (426) and the Free Wheel (425) help maintain proper gear engagement between the Rack (416) and the Pinion Gear (423).

The pinion gear 423 may be driven by the Rack (416) to rotationally oscillate or reversibly rotate the pinion gear 423 and the meshing gear 411, which is connected to the pinion gear 423. The meshing gear 411 may engage or be in contact with a driven gear 412 to rotationally oscillate or reversibly rotate the driven gear 412. The driven gear 412 causes rotational oscillation or reversible rotation of the Inner Tube (401) which is coupled to the driven gear 412. As a result, the rack and gear assembly causes oscillating rotation of the inner tube 401, such that the inner tube 401 rotates back and forth to produce a "sawing" type oscillating rotary cutting motion at its distal end.

The Pinion Gear (423)/Meshing Gear (411) assembly may rotate about a Gear Shaft (424). The gear shaft 424 may be held in place by the Hand Piece or handle (403) or features thereof. The outer diameter of the free wheel 425 contacts the Rack Columns (426) to maintain proper meshing between the Rack (416) and Pinion Gear (423). The inner diameter of the free wheel 425 is free to rotate about the Gear shaft (424). A Rack Column 426 includes a surface which is positioned parallel to the gear teeth on the Rack (416). The Rack Column 426 contacts the Free Wheel (425) to maintain proper positioning or engagement of the gear teeth of the rack 416 with the Pinion Gear (423).

In the various mechanism or device variations illustrated and described herein, e.g., the medical devices of FIGS. 8A-8E, 12A-14E, and 17, the vacuum or suction powered mechanism may include a shuttle valve 422, a drive piston or shaft 428 and a linkage or bi-stable switch 421. The mechanism may be coupled to a vacuum source. The linkage or bi-stable switch 421 may be responsible for reversing vacuum or suction air flow through mechanism to prevent unstable shuttle valve (422) fluttering. The shuttle valve 422 controls the airflow through the vacuum or suction powered mechanism by alternately venting one side of a vacuum or suction powered mechanism while evacuating the opposite side.

The vacuum powered mechanism for use in any of the devices and mechanism/component arrangements described herein may include a drive shaft 428 or drive piston located in a chamber. The suction may be applied to both sides of a drive shaft 428 or drive piston in an alternating manner to cause the drive shaft 428 or drive piston to reciprocate between a drive stroke and a return stroke to create a reciprocating motion. The mechanism may include a shuttle body 422 or valve coupled to the drive shaft 428 by a linkage 421. The shuttle body 422 or valve may be moveable between a forward and return position, where movement between the forward and return positions alternates a fluid path between the chamber and vacuum source (supplied to the mechanism via vacuum port 430) so that during application of suction or vacuum from the vacuum source, movement of the shuttle body 422 or valve causes the drive shaft 428 to cycle between the drive stroke and the return stroke, creating a reciprocating motion which causes reciprocation of various components, e.g., a crank arm or a rack.

The linkage 421 may couple the drive shaft 428 to the shuttle body 422 or valve such that as the drive shaft 428 approaches the end of the drive or return stroke the linkage 421 transfers a force to the shuffle body 422 or valve to assist in switching between the forward and return positions and prevents or minimizes unstable flutter of the shuttle body 422 or valve between the forward and return positions.

Optionally, other vacuum powered mechanisms may be utilized in the devices described herein, e.g., a mechanism including a poppet valve which alternates evacuation and venting of the mechanism may be used. Optionally, in any of the devices described herein, the mechanism may be powered solely by suction, e.g. suction created by a vacuum source, where no other power source, e.g., electric or pneumatic, is necessary to power the device.

In certain variations, with respect to any of the oscillating medical devices or cutting devices described herein, the cutter may oscillate or reversibly rotate over various arc ranges, e.g., over an arc in the range of about 20 to about 360 degrees. In certain variations, with respect to any of the oscillating medical devices or cutting devices described herein, the cutter or operable element may cut tissue while preventing tissue breakage resulting from twisting of the tissue or the cutter or operable element may cut tissue while preventing twisting of the tissue.

Figure 15:
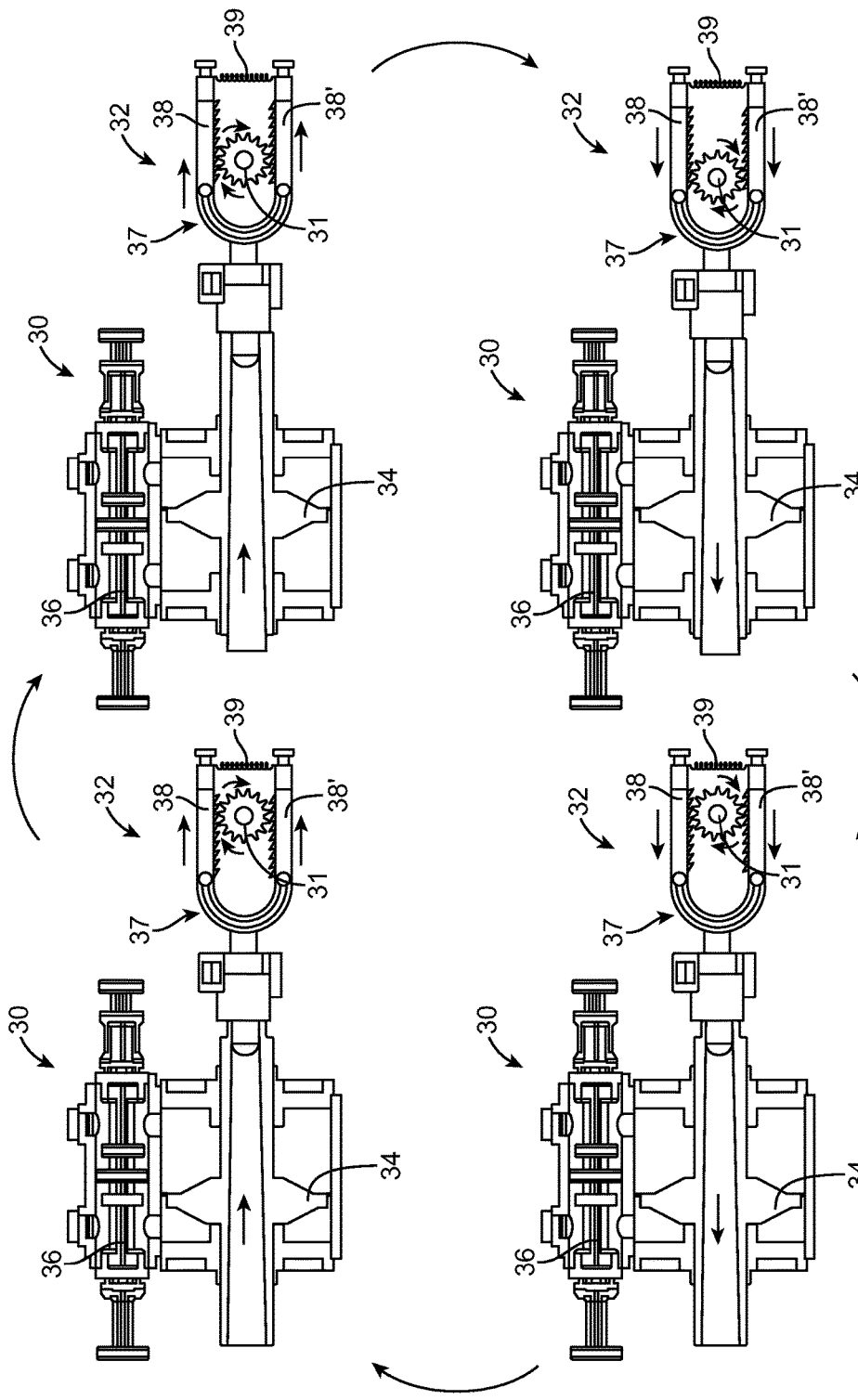
FIG. 15 shows a cross section of a variation of a vacuum or suction powered mechanism coupled to a component for converting linear reciprocating motion to rotational motion, including a rack and pinion gear with a spring ratchet mechanism.

FIG. 15 shows another variation of a mechanism powered by suction from a vacuum or suction source, where the mechanism is coupled to or includes a component for converting linear reciprocating motion to a rotating or rotary motion. The mechanism 30 may include a drive piston 34 and a shuttle piston 36. The drive piston 34 may be coupled or connected to a rack and pinion gear 32, where the rack includes a U-shaped rack assembly 37 with upper and lower racks or rack arms 38, 38'. The upper and lower rack arms 38, 38' may pivot and a spring 39 may be connected between the upper and lower rack arms 38, 38'. The mechanism 30 may drive a rotary output pinion gear 31 utilizing a spring ratchet mechanism. Optionally, the drive piston 34 may be coupled to an output shaft which is connected to or coupled to the rack and pinion gear.

Suction created by the vacuum or suction source causes the drive piston 34 to reciprocate linearly back and forth. The back and forth linear reciprocation of the drive piston 34 causes the U-shaped rack 37 to reciprocate linearly back and forth. Optionally, the drive piston 34 may cause an output shaft to reciprocate linearly back and forth, which causes the U-shaped rack 37 to reciprocate linearly back and forth. The U-shaped rack 37 includes an upper rack 38 and a lower rack 38'. The upper rack 38 may include ratcheting teeth that are set at an angle such that the upper rack 38 may engage and drive the pinion gear 31 when the U-shaped rack assembly 37 is driven from a proximal position to a distal position (left to right when viewing the figures). When the rack assembly 37 is driven from left to right, the teeth on the upper rack 38 engage the teeth on the pinion gear 31 while the teeth on the lower rack 38' slip past the teeth on the pinion gear 31, thereby causing the pinion gear 31 to rotate clockwise.

The lower rack 38' may include ratcheting teeth that are set at an angle such that the lower rack 38' may engage and drive the pinion gear 31 when the rack assembly 37 is driven from a distal position to a proximal position (right to left when viewing the figures). When the rack assembly 37 is driven from a distal position to a proximal position (right to left when viewing the figures), the teeth on the lower rack 38' engage the teeth on pinion gear 31, while the teeth on the upper rack 38 slip past the teeth on the pinion gear 31, thereby causing the pinion gear 31 to rotate clockwise. The upper and lower rack anus 38, 38' may pivot (e.g., separately or together) to allow engagement and disengagement with the pinion gear 31 as the rack assembly 37 changes direction. A spring 39 may be connected or assembled to or between the pivoting upper and lower racks 38, 38' or arms to dispose the racks in contact with the pinion gear 31 at all times or substantially all the time. The spring 38 may serve to engage the teeth of a driving rack with the teeth on the pinion gear while the opposite rack is disengaged from the teeth on the pinion gear. The linear reciprocating back and forth motion of the mechanism 30 causes the pinion gear 31 to rotate, thereby generating or producing a rotating motion or converting the linear reciprocation motion into rotating motion. The produced rotational motion may cause an output shaft or other tool of a device to rotate, e.g., an output shaft which performs work on a tissue or causes a tool to perform work on tissue. An alternative variation may include a flywheel or flywheel type of mechanism to maintain smooth, continuous, rotary motion of an output shaft or tool.

The pinion gear 31 may rotate in only one direction as determined by the direction that the teeth are set on the racks and pinion gear. While the rack assembly 37 and pinion gear 31 are configured or designed for driving and rotating the pinion gear 31 in the clockwise direction in this example shown in FIG. 15, it is contemplated that the rack assembly 37 and pinion gear 31 could be configured or designed for driving and rotating the pinion gear 31 in the counterclockwise direction. This would be possible by reversing the direction of the teeth on the upper and lower racks and/or the teeth on the pinion gear.

Figure 16:
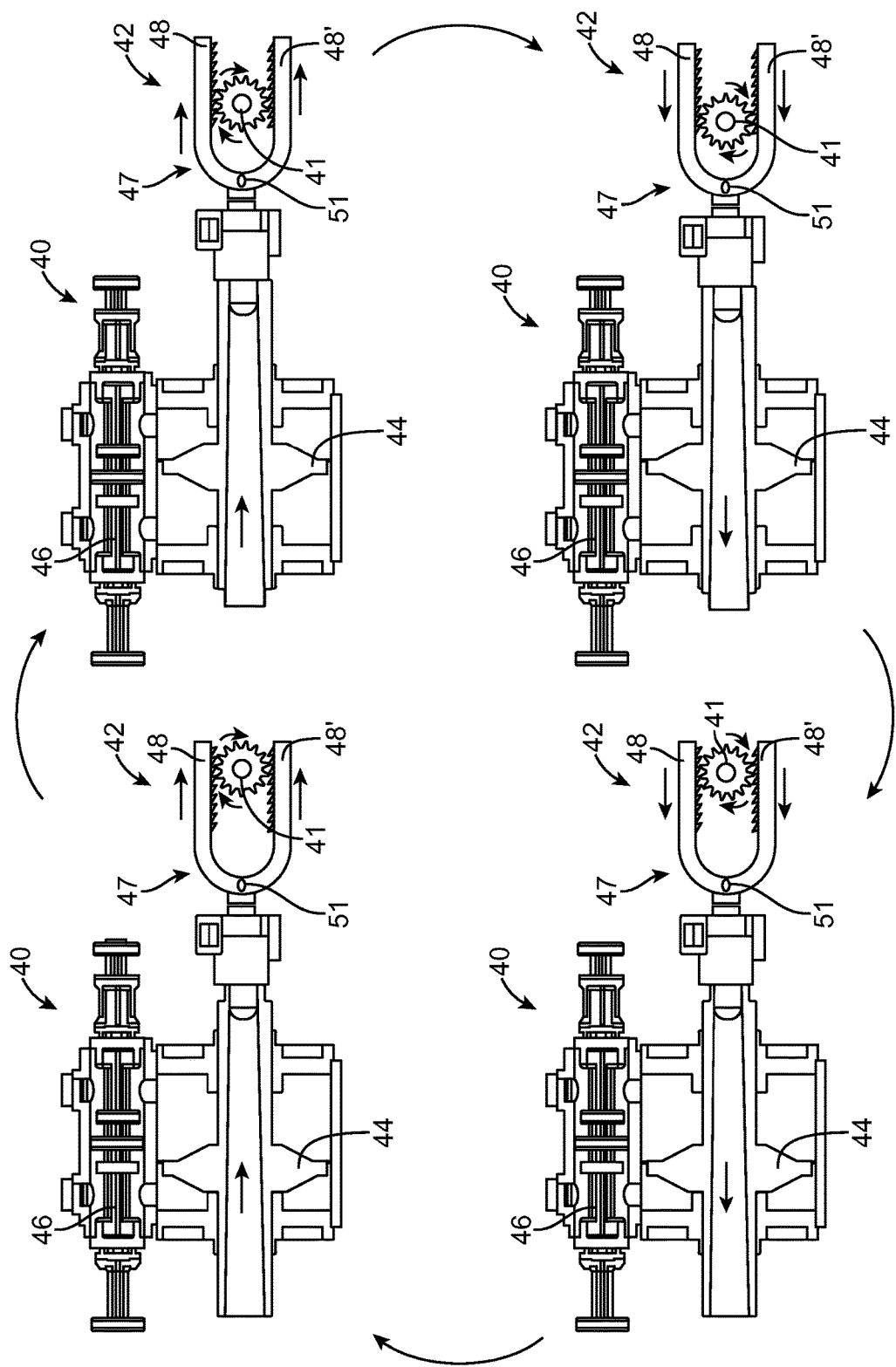
FIG. 16 shows a cross section of a variation of a vacuum or suction powered mechanism coupled to a component for converting linear reciprocating motion to rotational motion, including a rack and pinion gear with a pivoting rack assembly.

FIG. 16 shows another variation of a mechanism powered by suction from a vacuum or suction source, where the mechanism is coupled to or includes a component for converting linear reciprocating motion to a rotating or rotary motion. The mechanism 40 may include a drive piston 44 and a shuttle piston 46. The drive piston 44 may be connected to or coupled to a rack and pinion gear 42, where the rack includes a U-shaped rack assembly 47 with upper and lower racks or rack arms 48, 48'. The U-shaped rack assembly 47 may pivot to allow the upper and lower racks 48, 48' to alternately engage the pinion gear 41 depending on the direction the rack assembly 47 is moving. The non-driving rack or teeth may act to push the teeth on the opposite, driving rack into the pinion gear 41 to engage the pinion gear teeth with the driving rack teeth. The pivot 51 may be located between the upper and lower racks 48, 48 to allow the U-shaped rack assembly 47 to pivot as a whole. The mechanism 40 may drive the rack and pinion gear 42 to generate rotating motion, where the mechanism 40 drives a rotary output pinion gear 41 with a pivoting rack and gear mechanism. Optionally, the drive piston 44 may be coupled to an output shaft which is connected to or coupled to the rack and pinion gear 42.

Suction created by the vacuum or suction source causes the drive piston 44 to reciprocate linearly back and forth. The back and forth linear reciprocation of the drive piston 44 of the mechanism 40 causes the U-shaped rack assembly 47 to reciprocate linearly back and forth. Optionally, the drive piston 44 may cause an output shaft to reciprocate linearly back and forth, which causes the U-shaped rack assembly 47 to reciprocate linearly back and forth. The U-shaped rack assembly 47 includes an upper rack 48 and a lower rack 48'. The upper rack 48 may include ratcheting teeth that are set at an angle such that the upper rack 48 may engage and drive the pinion gear 41 when the U-shaped rack assembly 47 is driven from a proximal position to a distal position (left to right when viewing the figures). When the rack assembly 47 is driven from left to right, the teeth on the upper rack 48 engage the teeth on the pinion gear 41 while the teeth on the lower rack 48' slip past the teeth on the pinion gear 41, thereby causing the pinion gear 41 to rotate clockwise.

The lower rack 48' may include ratcheting teeth that are set at an angle such that the lower rack 48' may engage and drive the pinion gear 41 when the rack assembly 47 is driven from a distal position to a proximal position (right to left when viewing the figures). When the rack assembly 47 is driven from a distal position to a proximal position (right to left when viewing the figures), the teeth on the lower rack 48' engage the teeth on pinion gear 41, while the teeth on the upper rack 48 slip past the teeth on the pinion gear 41, thereby causing the pinion gear 41 to rotate clockwise. The U-shaped rack assembly 47 pivots to allow alternating engagement and disengagement between the upper rack teeth and the lower rack teeth with the pinion gear 41 as the rack assembly 47 changes direction. The linear reciprocating back and forth motion of the mechanism 40 causes the pinion gear 41 to rotate, thereby generating or producing a rotating motion or converting the linear reciprocation motion into rotating motion. The produced rotational motion may cause an output shaft or tool of a device to rotate, e.g., an output shaft which performs work on a tissue or causes a tool to perform work on tissue.

The pinion gear 41 may rotate in only one direction as determined by the direction the teeth are set on the racks and pinion gear. While the rack assembly 47 and pinion gear 41 are configured or designed for driving and rotating the pinion gear 41 in the clockwise direction in this example shown in FIG. 16, it is contemplated that the rack assembly 47 and pinion gear 41 could be configured or designed for driving and rotating the pinion gear 41 in the counter-clockwise direction. This would be possible by reversing the direction of the teeth on the upper and lower racks and/or the teeth on the pinion gear.

Optionally, in certain variations of the mechanisms described herein, the various racks may be integrated with a drive piston or separate and coupled or connected to a drive piston.

As described supra, certain variations of vacuum or suction powered devices may produce rotary or rotational motion, however, in certain variations, the mechanism may not produce rotational motion directly, but rather indirectly, e.g., by creating or producing a linear reciprocating motion which is translated into a rotary or rotational motion by utilizing any of the various mechanisms and/or components described herein.

Optionally, a drive piston may be directly coupled to any of the components described above, for example, without the use of an output shaft. Optionally, a mechanism may be configured to produce rotational or rotary motion directly.

In certain variations, the various mechanisms described herein may include a bi-stable switch or linkage coupling the drive piston and shuttle body to ensure a reliable transition of the shuttle body or a valve on the shuttle body past or completely past a vacuum supply port to prevent unstable flutter of the shuttle body and possible mechanism or motor stall.

In certain variations, any of the mechanisms described herein may include a drive shaft or drive piston located in a chamber. The suction may be applied to both sides of a drive shaft or drive piston in an alternating manner to cause the drive shaft or drive piston to reciprocate between a drive stroke and a return stroke to create a reciprocating motion. The mechanism may include a shuttle body or valve coupled to the drive shaft by a linkage. The shuttle body or valve may be moveable between a forward and return position, where movement between the forward and return positions alternates a fluid path between the chamber and vacuum source so that during application of suction or vacuum from the vacuum source movement of the shuttle body or valve causes the drive shaft to cycle between the drive stroke and the return stroke.

The linkage may couple the drive shaft to the shuttle body or valve such that as the drive shaft approaches the end of the drive or return stroke the linkage transfers a force to the shuttle body or valve to assist in switching between the forward and return positions and prevents or minimizes unstable flutter of the shuttle body or valve between the forward and return positions. A mechanism having a shuttle body, drive piston and linkage arrangement are shown in various devices, e.g., the devices shown in FIGS. 8A-8E, 12A-14E and may be utilized as the mechanism in an of the other mechanism or mechanism/component arrangements illustrated in any of the other figures provided herein or described herein.

In certain variations, in any of the medical devices described herein, a device may include at least one electrical conductor positioned on a patient contact portion of the device, where electrical energy from the conductor may be used to cauterize tissue or to ablate tissue. In another variation, a device may include at least one electrical conductor having at least one electrically resistive electrode positioned on a patient contact portion of the device, where the electrical energy causes heating of the electrode to a temperature adequate to cauterize tissue or where the electrical energy causes heating of the electrode to a temperature adequate to ablate tissue. In another variation, a device may include at least one electrical conductor positioned on a patient contact portion of the device wherein monopolar electrical energy may be conducted between the electrical conductor and a grounding pad positioned at a remote location on the patients' body and the energy may be used to cauterize tissue or the energy may be used to ablate tissue. In another variation, a device may include at least two electrical conductors positioned on a patient contact portion of the device where bipolar electrical energy may be conducted between the electrical conductors and the energy may be used to cauterize tissue or the energy may be used to ablate tissue. In another variation, a device may include at least one electrical conductor positioned on a patient contact portion of the device and wherein electrical energy may be conducted to a resistor where the resistor heats to a temperature that is sufficient to cauterize tissue or where the resistor heats to a temperate that is sufficient to ablate tissue.

In certain variations, a method of powering a medical device may include: providing suction created by a vacuum source to the medical device; applying the suction to both sides of a piston within the medical device in an alternating manner to cause the piston to reciprocate in a linear manner, wherein the piston is reciprocated solely by the applied suction; and converting the linear reciprocating motion into a rotary motion, which causes a shaft or tool of the medical device to rotate whereby the tool may perform work on a target tissue.

In certain variations, a method for removing tissue from the human body may include one or more of the following steps. A cutting device may be advanced next to a target tissue. The target tissue may be opposed, apposed or positioned against a cutting surface of the cutting device. The cutting device may produce or create an oscillating rotary motion to cause oscillating rotary motion of the cutting surface. The tissue may be cut with the oscillating rotary cutting, surface while cut tissue is not twisted or broken as a result of twisting within the cutting tube because the cutting tube oscillates about an arc of rotation rather than continuous rotations. Therefore, tissue twisting and/or resulting breakage may be avoided or prevented as the tissue is cut and/or withdrawn through a lumen of the cutting device by cutting the tissue with the oscillating rotary cutting surface.

In certain variations, the cutting device may produce linear reciprocating motion and convert linear reciprocating motion to oscillating rotary motion to cause oscillating rotary motion of the cutting surface. A grasping tool may be advanced through a lumen of the cutting device to grasp the target tissue and retract the target tissue proximally to appose or place the target tissue against the cutting surface of the cutting device. The tissue may be withdrawn through the lumen by using the grasping tool or by evacuating the tissue through the lumen with suction.

Any of the vacuum powered oscillating cutting devices described herein, e.g., as illustrated in FIGS. 12A-14E, may cut tissue while avoiding or preventing twisting of the tissue during cutting and/or withdrawing of the tissue or while preventing tissue breakage resulting from twisting of the tissue during cutting and/or twisting of the tissue. Alternatively, a cutting device for use in the methods described above may be powered using other sources of power or mechanisms, e.g., electrical power, pneumatic power, etc., where the device may cut tissue while avoiding or preventing twisting of the tissue during cutting, and/or withdrawing of the tissue or while preventing tissue breakage resulting from twisting of the tissue during cutting and/or twisting of the tissue.

In certain variations the cutting device does not require a tissue guide to avoid tissue twisting. In another variation, the cutting device includes a cutting tube and the cutting device does not require a stationary tube positioned within the cutting tube to avoid tissue twisting or breaking. A cutting, tube may be driven by a rack and pinion gear or other suitable mechanism that will cause the cutter to oscillate or reversibly rotate, e.g., over an arc in the range of 20-360 degrees. The oscillating cutting device does not require a stationary inner tube to prevent the tissue from twisting or breaking because the device "saws" the tissue instead of cutting with a continuously rotating cutting tube.

In certain variations, the cutting device may produce an oscillating rotary motion of the cutting surface such that the cutting surface cuts tissue while preventing tissue breakage resulting from twisting of the tissue. The cutting device may produce a linear reciprocating motion and convert the linear reciprocating motion to an oscillating rotary motion of the cutting surface such that the cutting surface cuts tissue while preventing tissue breakage resulting from twisting of the tissue. The cutting device may be powered by a vacuum powered mechanism configured to produce a linear reciprocating motion. A component having a rack and pinion gear assembly may be coupled to the mechanism and may convert the linear reciprocating motion to an oscillating rotary motion to cause oscillating rotary motion of the cutting surface such that the cutting surface cuts tissue without breaking the tissue resulting from twisting of the tissue.

Figure 17:
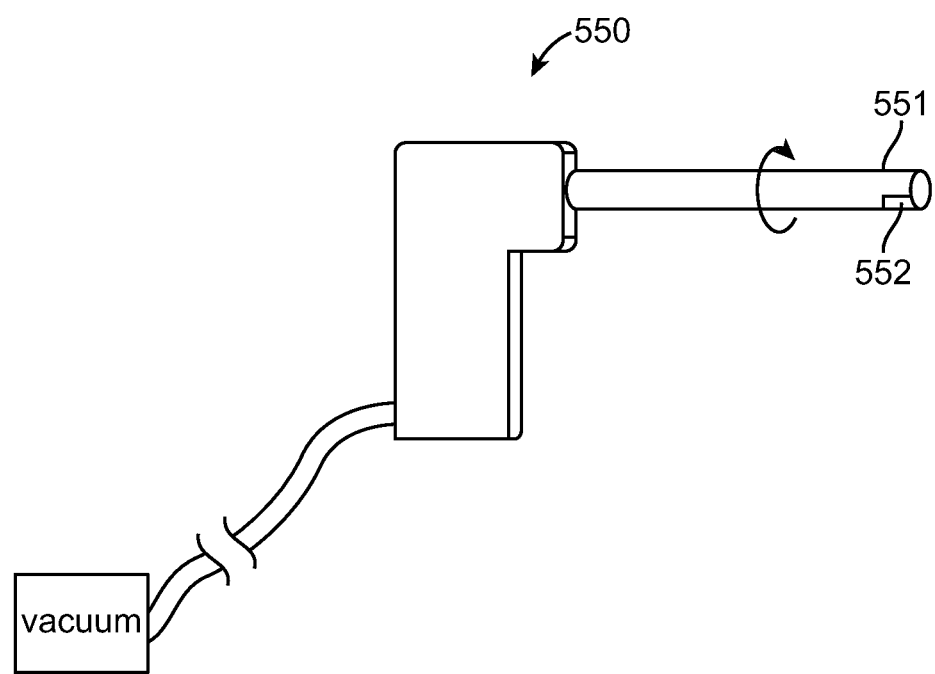
FIG. 17 illustrates a variation of a medical device having a rotating cutting tube or shaft where the device is powered by a vacuum powered mechanism.

Another example of a medical device 550 having a rotating cutting tube or shaft 551 where the device is powered by a vacuum powered mechanism and/or component as described herein is shown in FIG. 17. The device 550 could be connected to a vacuum or suction source for operation. The device may also include one or more electrical conductors 552 for cauterizing or ablating tissue. In certain alternative variations, optionally certain of the devices described herein may be modified or configured to produce direct rotary motion without requiring the conversion of linear motion to rotary motion.

In any of the various medical devices described herein, a filter mechanism may be utilized for collecting or filtering resected or cut tissue.

In certain variations, a filter mechanism may include a filter body and a filter lid. The filter body may include one or more tissue collection chambers, a bypass chamber and an exit port that serves as a connection point for the external source of suction. The filter lid may have two attachment points or ports for connecting tubing or a conduit. One attachment or port is located in a position such that fluid continuously flows through the filter lid and the filter body bypass chamber regardless of a filter lid (switch) position. This may be useful for connecting a section of tubing or conduit to perform a function that does not need the fluid medium to be filtered such as a connection to a vacuum powered motor or mechanism.

The other attachment port may be located in a position such that it can be moved over a bypass chamber or a collection chamber. The filter lid may be moved relative to the filter body to position tubing or conduit carrying excised tissue to any of the chambers in the filter body. When the tubing port carrying the excised tissue is positioned over the bypass chamber, the tissue and fluid medium flow through the bypass chamber and exit the device through the suction connection port.

When the tubing port carrying excised tissue is positioned over one of the collection chambers, the fluid medium passes through the filter and into the bypass chamber and then exits the device through the suction connection port. The tissue remains in the collection chamber where it may be collected for subsequent analysis.

Upon completion of the procedure, the filter mechanism, including the filter lid and filter body may be removed from the device. The tubing connections can be separated from the filter lid and render the device inoperable by making reassembly (and consequently, re-use) prohibitively difficult.

Optionally, the filter mechanism may be filled with tissue preservative, e.g., such as formalin, either by removing the filter lid from the body component, or by injecting the preservative through an opening in the filter mechanism. Plugs may be placed in the tubing ports in the filter lid and in the exit port to prevent the tissue preservative from leaking out of the filter mechanism.

The filter lid or other portion of the filter body may have features to store the plugs until they are ready for use. The filter lid may be removed from the filter body to expose a plurality of chambers to extract tissue from the tissue filter chamber for analysis.

The filter mechanism may have provisions to label the contents of the tissue collection chambers with information such as patient name, date of collection and the anatomical location that was sampled or type of tissue.

The tissue filter mechanism may be removed from a tissue resection device and used as a container to send tissue samples to a laboratory for analysis.

The filter mechanism may be integrated in or coupled to a vacuum or suction powered medical device or tissue resection or cutting or morscellating device, such as the devices described herein. The filter mechanism may also be integrated in or coupled to other medical devices, such as cutting or resecting devices, which are powered by electrical, pneumatic or other power sources.

In certain variations of the mechanisms or devices described herein, a vacuum powered mechanism may include a linkage or bi-stable switch may be manufactured using various materials that strain when the bi-stable switch is exposed to forces from the switch spring coupled thereto. For example, the linkage or switch may be made from plastic or other materials having similar properties. The bi-stable switch may be positioned within the chamber or handle of the device for storage and shipment such that features or support elements within the chamber or handle engage the switch and assume the stress from the switch spring, or biasing component, thereby relieving the stress from the bi-stable switch. The device may be configured such that after use, the bi-stable switch stops in a position where the bi-stable switch is not engaged with the support elements and not relieved of stress from the switch spring. As a result, the bi-stable switch is exposed to strain or stress from the switch spring or biasing component, which causes the linkage or switch to deform to a degree that the bi-stable switch no longer functions at some period of time after it is used. The deformed bi-stable switch may prevent re-use of the device, e.g., such that the device is suitable for single use, or may allow for a certain number of uses depending on the strength of the switch or linkage. A method of preventing reuse or for providing a certain number of use of a vacuum powered device described herein may include providing a deformable linkage or switch which deforms in an unsupported or strained position to render the mechanism inoperable.

The above arrangements, materials, and dimensions for the vacuum powered devices described herein are exemplary and are not intended to be limiting.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing, subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning, as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A method for performing work on tissue in the human body comprising:
   positioning an operable element located on a distal end of a medical device against a target tissue;
   powering the medical device with suction created by a vacuum source such that the suction drives a mechanism that produces linear reciprocating motion;
   converting the linear reciprocating motion into a rotary motion with a rack and pinion gear assembly, wherein the rack and pinion gear assembly comprises a rack and a pinion gear, wherein the rack is coupled to the mechanism such that linear reciprocating motion produced by the mechanism causes the rack to reciprocate, wherein the reciprocating rack drives the pinion gear in an oscillating rotary motion; and
   causing, via the rotary motion, the operable element to rotate, whereby the operable element performs work on the target tissue.

2. The method of claim 1, wherein the mechanism is powered solely by suction created by a vacuum source.

3. The method of claim 1, wherein the medical device produces an oscillating rotary motion.

4. The method of claim 1, further comprising at least one electrical conductor positioned on a patient contact portion of the device, wherein electrical energy from the conductor is used to cauterize tissue.

5. The method of claim 1, further comprising at least one electrical conductor positioned on a patient contact portion of the device, wherein electrical energy from the conductor is used to ablate tissue.

6. The method of claim 1, further comprising convening the linear reciprocating motion into a rotary motion with a rack and pinion gear assembly having a spring ratchet mechanism.

7. The method of claim 1, further comprising convening the linear reciprocating motion into a rotary motion with a rack and pinion gear assembly having a pivoting rack assembly.

8. The method of claim 1, further comprising applying the suction to both sides of a piston within the medical device in an alternating manner to cause the piston to reciprocate in a linear manner, wherein the piston is reciprocated solely by the applied suction.

9. A method for performing work on tissue in the human body comprising:
   positioning an operable element located on a distal end of a medical device against a target tissue;

powering the medical device with suction created by a vacuum source such that the suction drives a mechanism that produces linear reciprocating motion;

converting the linear reciprocating motion into a rotary motion with a component comprising a gear and a crank arm, wherein the gear is coupled to the mechanism via the crank arm and the linear reciprocating motion produced by the mechanism causes the crank arm to rotate the gear; and causing, via the rotary motion, the operable element to produce an oscillating rotary motion, whereby the operable element performs work on the target tissue.

10. The method of claim 9, wherein the mechanism is powered solely by suction created by a vacuum source.

11. The method of claim 9, further comprising at least one electrical conductor positioned on a patient contact portion of the device, wherein electrical energy from the conductor is used to cauterize tissue.

12. The method of claim 9, further comprising at least one electrical conductor positioned on a patient contact portion of the device, wherein electrical energy from the conductor is used to ablate tissue.

13. The method of claim 9, wherein the component further comprises a cam lobe coupled to the gear and a cam follower, wherein the cam follower is configured to exert a force on the cam lobe to cause the gear to translate into a position in which the vacuum powered mechanism is unlikely to stall.

14. The method of claim 13, wherein the gear is coupled to a shaft such that rotation of the gear causes rotation of the shaft.

15. A method for performing work on tissue in the human body comprising:

positioning an operable element located on a distal end of a medical device against a target tissue;

powering the medical device with suction created by a vacuum source such that the suction chives a mechanism that produces linear reciprocating motion;

converting the linear reciprocating motion into a rotary motion; and causing, via the rotary motion, the operable element to rotate, whereby the operable element performs work on the target tissue.

16. The method of claim 15, wherein the mechanism is powered solely by suction created by a vacuum source.

17. The method of claim 15, further comprising at least one electrical conductor positioned on a patient contact portion of the device, wherein electrical energy from the conductor is used to cauterize tissue.

18. The method of claim 15, further comprising at least one electrical conductor positioned on a patient contact portion of the device, wherein electrical energy from the conductor is used to ablate tissue.

19. The method of claim 15, further comprising converting the linear reciprocating motion into a rotary motion with at least one of a crank mechanism, an anti-stall crank mechanism, a rack and pinion gear assembly, a rack and pinion gear assembly having a spring ratchet mechanism, and a rack and pinion gear assembly having a pivoting rack assembly.

20. The method of claim 15, further comprising converting the linear reciprocating motion into a rotary motion with a component comprising a gear and a crank arm, wherein the gear is coupled to the mechanism via the crank arm and the linear reciprocating motion produced by the mechanism causes the crank arm to rotate the gear.

21. The method of claim 20, wherein the component further comprises a cam lobe coupled to the gear and a cam follower, wherein the cam follower is configured to exert a force on the cam lobe to cause the gear to translate into a position in which the vacuum powered mechanism is unlikely to stall.

22. The method of claim 21, wherein the gear is coupled to a shaft such that rotation of the gear causes rotation of the shaft.

23. The method of claim 15, further comprising applying the suction to both sides of a piston within the medical device in an alternating manner to cause the piston to reciprocate in a linear manner, wherein the piston is reciprocated solely by the applied suction.

* * * * *